(12) United States Patent
Johnson et al.

(10) Patent No.: US 9,422,236 B2
(45) Date of Patent: Aug. 23, 2016

(54) PHENICOL ANTIBACTERIAL AGENTS

(71) Applicant: Zoetis Services LLC, Florham Park, NJ (US)

(72) Inventors: Timothy Allan Johnson, Richland, MI (US); Rajendran Vairagoundar, Kalamazoo, MI (US); Richard Andrew Ewin, Kalamazoo, MI (US)

(73) Assignee: Zoetis Services LLC, Florham Park, NJ (US)

( * ) Notice: Subject to any disclaimer, the term of this patent is extended or adjusted under 35 U.S.C. 154(b) by 0 days.

(21) Appl. No.: 14/784,043

(22) PCT Filed: Apr. 16, 2014

(86) PCT No.: PCT/US2014/034336
§ 371 (c)(1),
(2) Date: Oct. 13, 2015

(87) PCT Pub. No.: WO2014/172443
PCT Pub. Date: Oct. 23, 2014

(65) Prior Publication Data
US 2016/0075647 A1    Mar. 17, 2016

Related U.S. Application Data

(60) Provisional application No. 61/812,869, filed on Apr. 17, 2013.

(51) Int. Cl.
| | |
|---|---|
| *C07D 213/56* | (2006.01) |
| *C07C 381/10* | (2006.01) |
| *A61K 31/44* | (2006.01) |
| *A61K 31/165* | (2006.01) |
| *C07D 213/71* | (2006.01) |
| *C07D 213/57* | (2006.01) |

(52) U.S. Cl.
CPC ............ *C07C 381/10* (2013.01); *C07D 213/56* (2013.01); *C07D 213/57* (2013.01); *C07D 213/71* (2013.01); *C07B 2200/07* (2013.01)

(58) Field of Classification Search
None
See application file for complete search history.

(56) References Cited

FOREIGN PATENT DOCUMENTS

| EP | 0 014 437 A2 | 8/1980 |
|---|---|---|
| WO | 03/077828 A2 | 9/2003 |
| WO | 2012/125832 A2 | 9/2012 |

*Primary Examiner* — Zinna Northington Davis
(74) *Attorney, Agent, or Firm* — Paul M. Misiak

(57) ABSTRACT

The present invention provides novel phenicol derivatives, their use for the treatment of infections in mammals, pharmaceutical compositions containing these novel compounds, and methods for the preparation of these compounds.

20 Claims, No Drawings

PHENICOL ANTIBACTERIAL AGENTS

CROSS-REFERENCE TO RELATED APPLICATIONS

This application is a US National Stage entry of International Application No. PCT/US2014/034336, filed Apr. 16, 2014, which claims the benefit of U.S. Provisional Application No. 61/812869, filed Apr. 17, 2013, now expired, the entire contents each of which are incorporated herein by reference.

FIELD OF THE INVENTION

The present invention provides novel phenicol derivatives, their use for the treatment of infections in mammals, pharmaceutical compositions containing these novel compounds, and methods for the preparation of these compounds.

BACKGROUND OF THE INVENTION

There is a growing need for new antibiotic agents for the treatment of bacterial infections in animals, and in particular there is a need for new agents which overcome increasing bacterial resistance to existing antibiotics.

Florfenicol is a broad spectrum phenicol antibiotic used exclusively in veterinary medicine. Phenicol antibiotics as a class are potent inhibitors of bacterial protein biosynthesis. Florfenicol has a broad spectrum of activity against many gram-negative and gram-positive bacteria, and is useful in the prevention and treatment of bacterial infections due to susceptible pathogens in birds, reptiles, fish, shellfish and mammals. An important use of florfenicol is in the treatment of respiratory infections in cattle, such as those caused by, for example, *Mannheimia haemolytica*, *Pasteurella multocida* and *Haemophilus somnus*. Effective treatment of bovine respiratory disease (BRD) plays a significant role in reducing what is otherwise one of the leading causes of economic loss to both the dairy and beef industries worldwide.

Reports in recent years indicate that bacterial resistance to florfenicol is developing and has been observed across multiple bacterial genera and species, such as *Salmonella* (Bolton, L. F., et al., Clin. Microbiol., 1999, 37, 1348), *E. coli* (Keyes, K., et al., Antimicrob. Agents Chemother., 2000, 44, 421), *Klebsiella pneumoniae* (Cloeckaert, A., et al., Antimicrob. Agents Chemother., 2001, 45, 2381), and in the aquacultural pathogen, *Photobacterium damselae* subsp. *piscicida* (formerly *Pasteurella piscicida*) (Kim, E., et al., Microbiol. Immunol., 1996, 40, 665). In light of the increasing threat of florfenicol resistance and the apparent mobility of the resistance genes across bacterial species and animal hosts (Cloeckaert, A., et al., Antimicrob. Agents Chemother., 2000, 44, 2858), there is an important need for new antibiotics that maintain or surpass the activity of florfenicol, while also overcoming the challenges of florfenicol resistance. The compounds of the present invention represent such an improvement.

SUMMARY OF THE INVENTION

The present invention provides for compounds of formula I

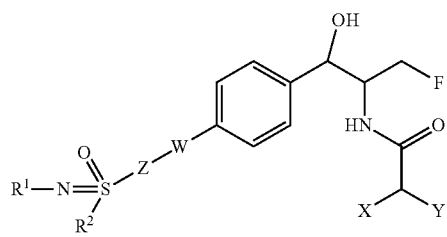

wherein $R^1$ is
 a) —H,
 b) —C(O)—$R^3$,
 c) —$C_1$-$C_6$ alkyl, or
 d) —CN;
$R^2$ is
 a) —$C_1$-$C_6$ alkyl optionally substituted with one to three halo, or
 b) —$C_3$-$C_6$ cyclopropyl;
$R^3$ is —$C_1$-$C_6$ alkyl;
W is

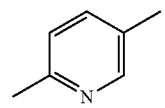

or
 b) absent;
X and Y are each independently halo;
Z is
 a) —$C_1$-$C_2$ alkyl-,
 b) —$C_3$-$C_4$ cycloalkyl- or
 c) absent;
or a pharmaceutical acceptable salt thereof.

More particularly, the present invention provides for compounds of formula I wherein X and Y are each chloro, or X and Y are each fluoro.

The present invention also provides for compounds of formula I wherein W is

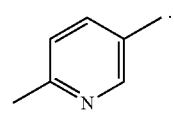

Thus, the present invention provides for compounds of formula II

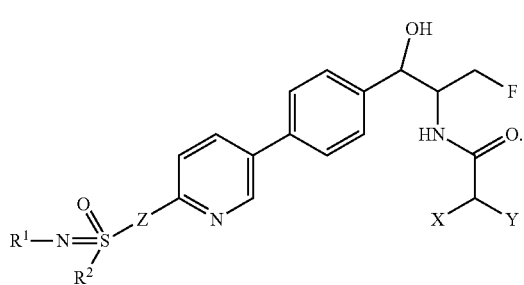

More particularly, the present invention provides for compounds of formula II wherein $R^1$ is —H or —CN, $R^2$ is —CH$_3$, and Z is —CH$_2$— or absent.

Also, the present invention provides for compounds of formula I wherein W is absent and Z is absent.

Thus, the present invention provides for compounds of formula III

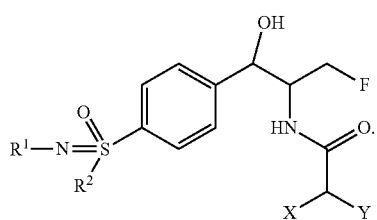

More particularly, the present invention provides for compounds of formula III wherein $R^1$ is —H or —CN and $R^2$ is —CH$_3$ or —CH$_2$—F.

Also, the present invention provides for compounds of formula I wherein
W is

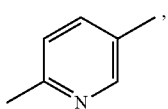

Z is absent, $R^1$ is —H, and $R^2$ is —CH$_3$.

Thus, the present invention provides for compounds of formula IV

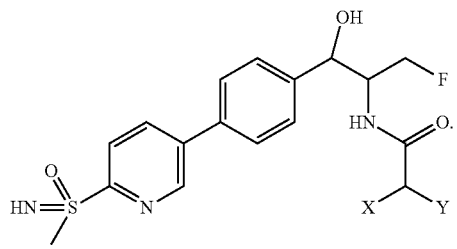

More particularly, the present invention provides for compounds of formula IV wherein X and Y are each chloro or X and Y are each fluoro.

In another aspect, the present invention also provides for:
pharmaceutical compositions which comprise a pharmaceutically acceptable carrier and a compound of formula I (including compounds of formula II, III and IV);
methods for controlling or treating infections in mammals by administering to a mammal in need of a therapeutically effective amount of a compound of formula I (including compounds of formula II, III and IV) or a pharmaceutically acceptable salt thereof;
methods for controlling or treating infections in livestock and companion animals by administering to an animal in need thereof a therapeutically effective amount of a compound of formula I (including compounds of formula II, III and IV) or a pharmaceutically acceptable salt thereof; and
methods for the preparation of compounds of the present invention.

DETAILED DESCRIPTION

With respect to the above compound, and throughout the application and claims, the following terms have the meanings defined below.

The term "halo" refers to chloro, bromo, fluoro, and iodo.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-4}$ alkyl refers to alkyl of one to four carbon atoms, inclusive; $C_{1-6}$ alkyl refers to alkyl of one to six carbon atoms, inclusive; and $C_{1-8}$ alkyl refers to alkyl of one to eight carbon atoms, inclusive.

The term alkyl refers to straight, branched and a cyclic saturated monovalent hydrocarbon groups, but reference to an individual radical such as "propyl" embraces only the straight chain radical, a branched chain isomer such as "isopropyl" or a cyclic isomer such as cyclopropylmethyl or cyclopentyl being specifically referred to.

The term "cycloalkyl" refers to a mono ring such as cyclopropyl, cyclobutyl, cyclopentyl, or cyclohexyl.

The term "Het" refers to saturated or unsaturated monocyclic or bicyclic heterocyclics, containing at least one heteroatom selected from N, O, and S. Bicyclic heterocyclics rings may be fused, spiro, or bridged ring systems. Monocyclic heterocyclic rings contain from 4- to 10-ring atoms, preferably from 5 to 6 member atoms in the ring. Bicyclic heterocyclics contain from 7 to 14 member atoms, preferably 9 to 12 member atoms in the ring. Examples of heterocyclic groups include, but are not limited to, substituted or unsubstituted tetrahydrofuran, dioxane, pyrrolidine, piperidine, piperazine, tetrahydrotriazine, tetrahydropyrazole, tetrahydrothiophene, dihydro-1,3-dithiol-2-yl, hexahydrothiepin-4-yl, thienyl, furanyl, pyrrolyl, imidazolyl, pyrazolyl, thiazolyl, isothiazolyl, oxazolyl, isoxazolyl, triazolyl, tetrazolyl, pyridinyl, pyrazinyl, pyridazinyl, pyrimidinyl, piperidinyl, pyrrolidinyl, piperazinyl, azetidinyl, aziridinyl, morpholinyl, thietanyl, oxetaryl, thiophenyl, thiadiazolyl, oxadizolyl. Examples of suitable bicyclic heterocyclic groups include, but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 5-4H-imidazo[4,5-d]thiazolyl, 3-, 5-, or 8-pyrazino[2,3-d]pyridazinyl, 2-, 3-, 5-, or 6-imidazo[2,1-b]thiazolyl, imidazo[1,2-a]pyridinyl, thiazolo[5,4-b]pyridinyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]-benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

For heterocyclic groups containing sulfur, the oxidized sulfur such as SO or $SO_2$ groups are also included.

For heterocyclic groups containing nitrogen, nitrogen groups such as N→O or NH are also included.

At each occurrence, Het is optionally substituted with one to three OH, halo, —CN, —$NO_2$, $C_{1-6}$alkyl, —$C_{3-6}$cycloalkyl, oxo (=O), —$NH_2$, —$NHC_{1-4}$alkyl, —$N(C_{1-4}$alkyl$)_2$, —$OC_{1-4}$alkyl, —SH, —$SC_{1-4}$alkyl, —S(C=O)$C_{1-4}$alkyl, —$SONC_{1-4}$alkyl, —C(=O)$C_{1-4}$ alkyl, —C(=O)$NH_2$, —C(=O)$NHC_{1-4}$alkyl, —C(=O)N($C_{1-4}$alkyl$)_2$, —NC(=O)$NH_2$, —NC(=O)$NHC_{1-4}$alkyl, or NC(=O)N($C_{1-4}$alkyl$)_2$.

The term "mammal" refers to human or animals including livestock and companion animals. The phrase "companion animal" or "companion animals" refers to animals kept as pets. Examples of companion animals include cats, dogs, and horses. The term "livestock" refers to animals reared or raised in an agricultural setting to make products such as food or fiber, or for its labor. In some embodiments, livestock are suitable for consumption by mammals, for example humans. Examples of livestock animals include mammals, such as cattle, goats, horses, pigs, sheep, including lambs, and rabbits, as well as birds, such as chickens, ducks and turkeys. Specifically, livestock animals of the present invention refer to cattle and pigs. The compounds of the present invention may also be useful in aquaculture, such as fish.

The term "controlling", "treating" or "treatment" of a disease includes: (1) preventing the disease, i.e. causing the clinical symptoms or signs of the disease not to develop in a mammal that may be exposed to or predisposed to the disease but does not yet experience or display symptoms/signs of the disease; (2) inhibiting the disease, i.e., arresting or reducing the development of the disease or its clinical symptoms/signs; or (3) relieving the disease, i.e., causing regression of the disease or its clinical symptoms/signs.

The term "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "pharmaceutically acceptable" means suitable for use in mammals, companion animals or livestock animals.

The term "prodrug" refers to a bio-reversible derivative of a molecule, i.e. a compound of formula I of the present invention. Prodrugs can alter the solubility, lipophilicity and in-vivo distribution of drugs. By deliberately altering these key properties, it may be possible to improve absorption, enhance onset time, reduce first pass metabolism, allow development of aqueous IV formulations and achieve targeted delivery. In addition, prodrugs are useful in improving transdermal delivery, masking taste, minimizing pain on injection, improving stability, etc. In situations where the pharmacophore itself leads to poor delivery properties, prodrugs are one of the few strategies that can be used to salvage the highly active compound. Included within the scope of the present invention are all prodrugs of the compounds of formula I that can be prepared by the standard methods known to one skilled in the art. Prodrugs of the compounds of formula I may be prepared following the methods described in "Prodrugs of phosphates, phosphonates, and phosphinates," Krise J P, Stella V J, Advanced Drug Delivery Reviews, 19: (2) 287-310 May 22, 1996; "Targeted Prodrug Design to Optimize Drug Delivery". Hyo-Kyung Han and Gordon Amidon, AAPS PharmSci 2000; 2 (1) article 6; "Prodrugs", L. Prokai and K. Prokai-Tatrai, Chapter 12 in "Injectable Drug Development: Techniques to Reduce Pain and Irritation, Interpharm Press, Buffalo Grove, Ind., 1999; "Improved oral drug delivery: Solubility limitations overcome by the use of prodrugs", Fleisher D, Bong R, Stewart B H, Advanced Drug Delivery Reviews, 19: (2) 115-130 May 22, 1996; or "Preparation and hydrolysis of water soluble, non-irritating prodrugs of pharmaceuticals with oxaalkanoic acids," Crooks, Peter Anthony; Cynkowski, Tadeusz; Cynkowska, Grazyna; Guo, Hong; Ashton, Paul, PCT Int. Appl. (2000), 65 pp. Examples of representative prodrugs include phosphates, phosphonates, phosphinates, carboxylic esters and carbamates.

Compounds that have the same molecular formula but differ in the nature or sequence of bonding of their atoms or the arrangement of their atoms in space are termed "isomers".

Included within the scope of the described compounds are all isomers (e.g. cis-, trans-, enantiomers, or diastereomers) of the compounds described herein alone as well as any mixtures. All of these forms, including enantiomers, diastereomers, cis, trans, syn, anti, solvates (including hydrates), tautomers, and mixtures thereof, are included in the described compounds.

A specific value for X is halo.
A specific value for Y is halo.
A specific value for X and Y is chloride.
A specific value for X and Y is fluoride.

Examples of compounds of the present invention include the following: 2,2-difluoro-N-((1R,2S)-3-fluoro-1-hydroxy-1-(4-(6-(S-methylsulfonimidoyl)-pyridin-3-yl)phenyl)propan-2-yl)acetamide and 2,2-difluoro-N-((1R,2S)-3-fluoro-1-hydroxy-1-(4-(6-(S-methylsulfonimidoyl)-pyridin-3-yl)phenyl)propan-2-yl)acetamide.

The reaction schemes below illustrate the general synthetic procedures of the compounds of the present invention. All starting materials are prepared by procedures described in these schemes or by procedures known to one of ordinary skill in the art.

Pharmaceutical Salts

The compound of formula I may be used in its native form or as a salt. In cases where forming a stable nontoxic acid or base salt is desired, administration of the compound as a pharmaceutically acceptable salt may be appropriate. Pharmaceutically acceptable salts of the compounds of formula I include the acetate, ascorbate, aspartate, benzoate, besylate, bicarbonate/carbonate, bisulphate/sulphate, borate, camsylate, citrate, edisylate, etoglutarate, esylate, formate, fumarate, gluceptate, gluconate, glucuronate, glycerophosphate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Composition/Formulation

Pharmaceutical compositions of the present invention may be manufactured by processes well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more pharmaceutically acceptable carriers comprising excipients and auxiliaries, which facilitate processing of the active compound into preparations, which can be used pharmaceutically. Proper formulation is dependent upon the route of administration chosen. Pharmaceutically acceptable excipients and carriers are generally known to those skilled in the art and are thus included in the instant invention. Such excipients and carriers are described, for example, in "Remington's Pharmaceutical Sciences", Mack Pub. Co., New Jersey (1991).

The formulations of the invention can be designed to be short-acting, fast-releasing, long-acting, extended-releasing, or controlled-releasing. Specifically, the formulation of the invention can be an extended release form. Thus, the pharmaceutical formulations can also be formulated for controlled release or for slow release.

Dosage

Pharmaceutical compositions suitable for use in the present invention include compositions wherein the active ingredients are contained in an amount sufficient to achieve the intended purpose, i.e., control or the treatment of infections. More specifically, a therapeutically effective amount means an amount of compound effective to prevent, alleviate or ameliorate symptoms/signs of infections or prolong the survival of the subject being treated.

The quantity of active component, which is the compound of this invention, in the pharmaceutical composition and unit dosage form thereof, may be varied or adjusted widely depending upon the manner of administration, the potency of the particular compound and the desired concentration. Determination of a therapeutically effective amount is well within the capability of those skilled in the art. Generally, the quantity of active component will range between 0.01% to 99% by weight of the composition.

Generally, a therapeutically effective amount of dosage of active component will be in the range of about 0.1 mg to about 100 mg/kg of body weight/day; for example, about 0.1 to about 50 mg/kg of body weight/day; and for example, about 5 to about 50 mg/kg of body weight/day; and, for example, about 20 to about 50 mg/kg of body weight/day. It is to be understood that the dosages may vary depending upon the requirements of each subject and the severity of the infections.

The desired dose may conveniently be presented in a single dose or as divided doses administered at appropriate intervals, for example, as two, three, four or more sub-doses per day. Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation. If desired, the daily dose may also be divided into multiple doses for administration, e.g., two to four times per day.

Medical and Veterinary Uses

Compounds of the present invention provides novel phenicol antibacterial agents for the treatment of bovine respiratory disease infections in cattle caused by Gram-negative respiratory pathogens, such as *M. haemolytica, P. multocida, H. somnus*, and *M. bovis*.

Antibacterial Assays

Compounds of the present invention are tested against an assortment of Gram-negative and Gram-positive organisms using the industrial standard techniques described in M31-A3. Performance Standards for Antimicrobial Disk and Dilution Susceptibility Tests for Bacteria Isolated from Animals; Clinical and Laboratory Standards Institute, Approved Standard-Third Edition. The compounds of the present invention demonstrate very good antibacterial activity against BRD pathogens, for example, *M. haemolytica, P. multo., H. somnus* and *M. bovis*.

EXAMPLES

The synthesis of compounds of the present invention is further illustrated by the following examples. The starting materials and various intermediates utilized in the examples may be obtained from commercial sources, or are readily prepared from commercially available organic compounds, using well-known methods to one skilled in the art. Additional compounds of the present invention can be prepared by using procedures described in the following references: N-acylation: Synthesis, (7), 879-887, 2002; Synlett, (3), 361-364, 2011; Advanced Synthesis & Catalysis, 355(8), 1490-1494, 2013; and N-alkylation: Journal of Organic Chemistry, 58(7), 1922-1923, 1993; Synthesis, (7), 879-887; 2002.

Example 1

Preparation of 2,2-difluoro-N-((1R,2S)-3-fluoro-1-hydroxy-1-(4-(6-(S-methylsulfonimidoyl)pyridin-3-yl)phenyl)propan-2-yl)acetamide

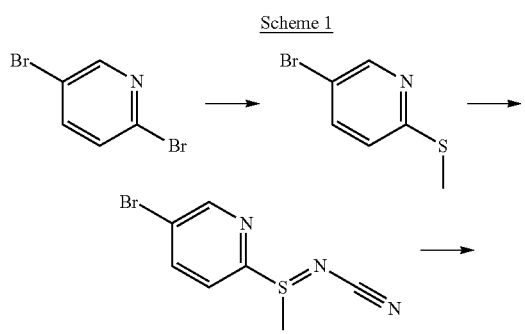

Scheme 1

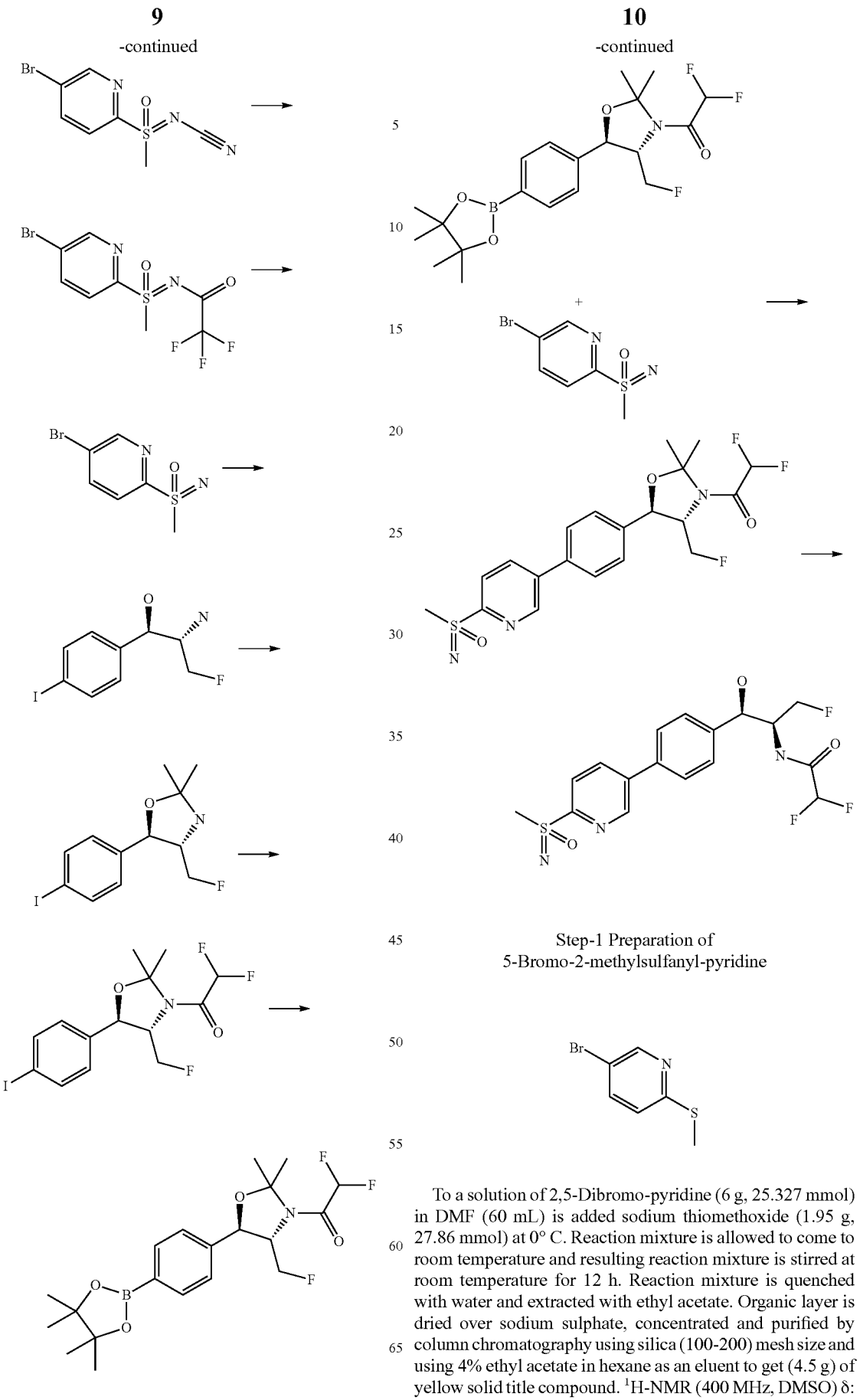

Step-1 Preparation of
5-Bromo-2-methylsulfanyl-pyridine

To a solution of 2,5-Dibromo-pyridine (6 g, 25.327 mmol) in DMF (60 mL) is added sodium thiomethoxide (1.95 g, 27.86 mmol) at 0° C. Reaction mixture is allowed to come to room temperature and resulting reaction mixture is stirred at room temperature for 12 h. Reaction mixture is quenched with water and extracted with ethyl acetate. Organic layer is dried over sodium sulphate, concentrated and purified by column chromatography using silica (100-200) mesh size and using 4% ethyl acetate in hexane as an eluent to get (4.5 g) of yellow solid title compound. $^1$H-NMR (400 MHz, DMSO) δ:

2.49 (s, 3H), 7.29 (d, 1H, J=8.76 Hz), 7.85-7.88 (dd, 1H, J1=2.44 Hz, J2=8.48 Hz), 8.55 (d, 1H, J=2.4 Hz). LC-MS (m/z): M+H=206.1.

Step-2 Preparation of 5-bromo-2-N-(cyano)methyl pyridine sulfilimine

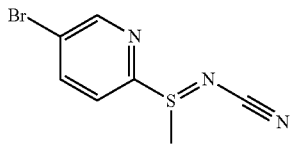

To a solution of 5-Bromo-2-methylsulfanyl-pyridine (4.5 g, 22.059 mmol) in methanol (50 mL) is added t-BuOK (2.965 g, 26.471 mmol), NH$_2$CN (50% aqueous solution) (2.638 g, 28.676 mmol) and NBS (5.89 g, 33.088 mmol) at 0° C. The resulting reaction mixture is stirred at 0° C. for 1 h. Solvent is evaporated in vacuo, reaction mixture is quenched with aqueous sodium metabisulphate solution and extracted with DCM. Organic layer is dried over sodium sulphate, concentrated and purified by silica gel column chromatography (100-200 mesh size) using 3% methanol in DCM as an eluent to give the title compound (4.7 g) as a yellow solid. LC-MS (m/z): M+H=243.8.

Step-3 Preparation of 5-bromo-2-N-(cyano)methyl pyridine sulfoximine

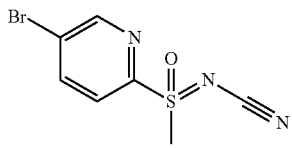

To a solution of 5-bromo-2-N-(cyano)methyl pyridine sulfilimine (4.7 g, 19.262 mmol) in ethanol (50 mL) is added K$_2$CO$_3$ (7.975 gm, 57.787 mmol) followed by mCPBA (6.645 μm, 38.525 mmol) at 0° C. The resulting reaction mixture is stirred at 0° C. for 10 h. Solvent is evaporated in vacuo, reaction mixture is quenched with water and extracted with DCM. Organic layer is dried over sodium sulphate, concentrated and purified by silica gel column chromatography (100-200 mesh size) using 50% ethyl acetate in n-Hexane as an eluent to give the title compound (2.1 g) as a yellow solid. $^1$H-NMR (400 MHz, DMSO) δ: 3.75 (s, 3H), 8.18 (d, 1H, J=8.44 Hz), 8.55-8.58 (dd, 1H, J1=2.2 Hz, J2=8.48 Hz), 9.09 (d, 1H, J=2.24 Hz), LC-MS (m/z): M+H=259.7.

Step-4 Preparation of 5-bromo-2-N-(trifluoroacetyl)methyl pyridine sulfoximine

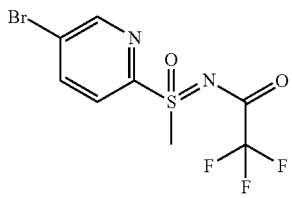 [SMILES: CS(=O)(=NC(=O)C(F)(F)F)c1ccc(Br)cn1]

To a solution of 5-bromo-2-N-(cyano)methyl pyridine sulfoximine (1 g, 3.846 mmol) in DCM (10 mL) is added Trifluoroacetic anhydride (1.615 mL, 11.538 mmol) at 0° C. Reaction mixture is allowed to stir at room temperature for 8 h. Excess of Trifluoroacetic acid and DCM is evaporated in vacuo. Reaction crude is taken in water and extracted with ethyl acetate. Organic layer is dried over sodium sulphate, concentrated and purified by silica gel column chromatography (100-200 mesh size) using 20% ethyl acetate in n-Hexane as an eluent to give (560 mg) the title compound as a yellow solid. $^1$H-NMR (400 MHz, DMSO) δ: 3.75 (s, 3H), 8.19 (d, 1H, J=8.44 Hz), 8.53-8.56 (dd, 1H, J1=2.32 Hz, J2=8.4 Hz), 9.03 (d, 1H, J=2.16 Hz). LC-MS (m/z): M+H=333.0.

Step-5 Preparation of 5-bromo-2-NH-methyl pyridine sulfoximine

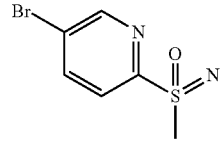

To a solution of 5-bromo-2-N-(Trifluoroacetyl)methyl pyridine sulfoximine (560 mg, 1.692 mmol) in Methanol (8 mL) is added K$_2$CO$_3$ (1167 mg, 8.459 mmol) at 0° C. Reaction mixture is allowed to stir at room temperature for 2 h. Solvent is evaporated in vacuo to give the title compound as a yellow solid (340 mg). $^1$H-NMR (400 MHz, DMSO) δ: 3.15 (s, 3H), 4.55 (bs, 1H), 8.0 (d, 1H, J=8.32 Hz), 8.35-8.38 (dd, 1H, J1=2.36 Hz, J2=8.44 Hz), 8.87 (d, 1H, J=2.08 Hz). LC-MS (m/z): M+H=237.0.

Step-6 Preparation of (4S,5R)-4-(fluoromethyl)-5-(4-iodophenyl)-2,2-dimethyloxazolidine

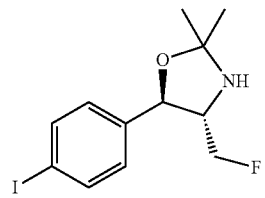 [SMILES: CC1(C)N[C@H](CF)[C@@H](c2ccc(I)cc2)O1]

Acetone (150 mL) is added to commercially available (1R, 2S)-2-amino-3-fluoro-1-(4-iodophenyl)propan-1-ol (15.0 g, 50.8 mmol). After stirring overnight at room temperature the solvent is removed under reduced pressure to give the title compound (17.6 g): m/z (Cl) M+H 335.

Step-7 Preparation of 2,2-difluoro-1-((4S,5R)-4-(fluoromethyl)-5-(4-iodophenyl)-2,2-dimethyloxazolidin-3-yl)ethanone

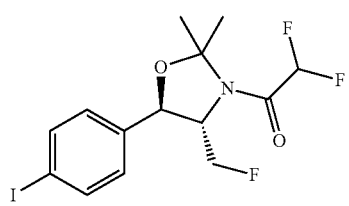 [SMILES: CC1(C)O[C@H](c2ccc(I)cc2)[C@@H](CF)N1C(=O)C(F)F]

To a stirring solution of the product of Step 6 (3.0 g, 8.9 mmol) in CH$_2$Cl$_2$ (50 mL) at 0° C. is added triethylamine (6.2 mL, 44.8 mmol) followed by dropwise addition of difluoroacetyl chloride (2.2 mL, 27.0 mmol). The reaction mixture is slowly allowed to warm to room temperature. After 1 hour the reaction mixture is diluted with water (75 mL) and extracted with CH$_2$Cl$_2$ (2×75 mL). The combined organic phase is dried over MgSO$_4$ and concentrated under vacuum. The crude material is chromatographed (80 g Redi-Sep column) eluting from 100% hexanes to 25:75 EtOAc:hexanes to afford the title compound (3.54 g): m/z (Cl) M+H 413.0.

Step-8 Preparation of 2,2-difluoro-1-((4S,5R)-4-(fluoromethyl)-2,2-dimethyl-5-(4-(4,4,5,5-tetramethyl-1,3,2-dioxaborolan-2-yl)phenyl)oxazolidin-3-yl)ethanone

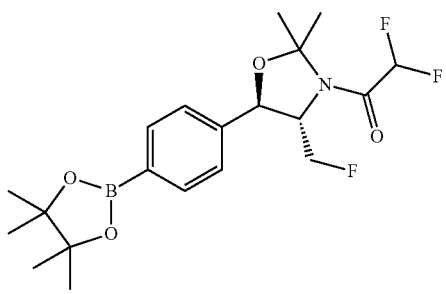 [SMILES: CC1(C)O[C@H](c2ccc(B3OC(C)(C)C(C)(C)O3)cc2)[C@@H](CF)N1C(=O)C(F)F]

To a solution of the product of Step 7 (3.5 g, 8.4 mmol) in dioxane (100 mL) is added bis(pinacolato)diboron (2.4 g, 9.3 mmol), potassium acetate (2.5 g, 25.4 mmol), and Pd (PPh$_3$)$_2$Cl$_2$ (300 mg, 0.4 mmol). The reaction is heated to 90° C. under nitrogen for 22 hours. Reaction mixture is cooled to room temperature and concentrated under vacuum to remove dioxane to a volume of ~50 mL. The residue is diluted with water (150 mL) and extracted with CH$_2$Cl$_2$ (2×125 mL). The combined organic phases are dried over Na$_2$SO$_4$ and concentrated under vacuum. The crude material is purified by chromatography (120 g Redi-Sep column) eluting from 100% hexanes to 25:75 EtOAc:hexanes to the title compound (2.06 g): m/z (Cl) M+H 413.2.

Step-9 Preparation of 2,2-difluoro-1-((4R,5R)-4-(fluoromethyl)-2,2-dimethyl-5-(4-(6-(methylsulfonimidoyl)pyridin-3-yl)phenyl)oxazolidin-3-yl)ethanone

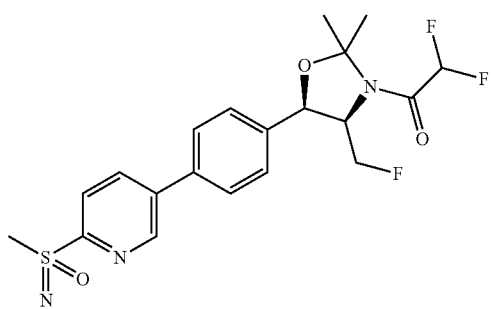 [SMILES: CC1(C)O[C@H](c2ccc(-c3ccc(S(C)(=N)=O)nc3)cc2)[C@H](CF)N1C(=O)C(F)F]

To a stirred solution of 2,2-Difluoro-1-{(4R,5R)-4-fluoromethyl-2,2-dimethyl-5-[4-(4,4,5,5-tetramethyl-[1,3,2]dioxaborolan-2-yl)-phenyl]-oxazolidin-3-yl}-ethanone (250 mg, 0.605 mmol) and 5-bromo-2-NH-methyl pyridine sulfoximine (170.70 mg, 0.726 mmol) in 1,4-Dioxane:water (5 mL:5 mL) is added K$_2$CO$_3$ (250.60 mg, 1.816 mmol) at room temperature. The resulting reaction mixture is degassed with nitrogen for 15 minutes then Pd(dppf)$_2$.Cl$_2$ (44.24 mg, 0.061 mmol) is added and heated to 80° C. for 8 h. Solvent is evaporated in vacuo and the crude material is diluted using water and extracted with ethyl acetate. Organic layer is dried over sodium sulphate, concentrated and purified by silica gel column chromatography (100-200 mesh size) using 2% methanol in DCM as an eluent to afford the title compound (250 mg) as yellow solid. LC-MS (m/z): M+H=442.1.

Step-10 Preparation of 2,2-difluoro-N-((1R,2S)-3-fluoro-1-hydroxy-1-(4-(6-(S-methylsulfonimidoyl)pyridin-3-yl)phenyl)propan-2-yl)acetamide

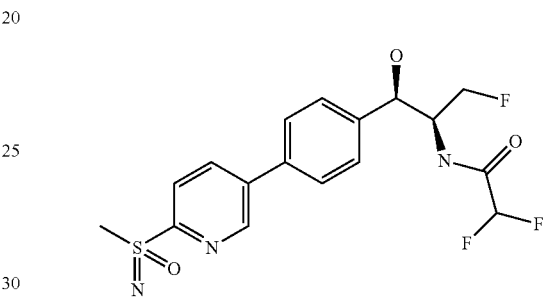

To a stirred solution of 2,2-difluoro-1-((4R,5R)-4-(fluoromethyl)-2,2-dimethyl-5-(4-(6-(methylsulfonimidoyl)pyridin-3-yl)phenyl)oxazolidin-3-yl)ethanone (250 mg, 0.567 mmol) in DCM (8 mL) is added TFA (1 mL) at 0° C. The reaction mixture is allowed to stir at room temperature for 4 h. Volatiles are removed under reduced pressure and crude is diluted using aqueous sodium bicarbonate and extracted with ethyl acetate. Organic layer is dried over sodium sulphate, concentrated and purified by silica gel column chromatography (100-200 mesh size) using 8% methanol in DCM as an eluent to afford the title compound (170 mg) as a brown solid. $^1$NMR (400 MHz, DMSO) δ: 3.19 (d, 3H, J=0.76 Hz), 4.32-4.37 (m, 1.5H), 4.42-4.46 (m, 0.5H), 4.48 (bs, 1H), 4.53-4.56 (m, 0.5H), 4.66-4.69 (m, 0.5H), 4.91 (t, 1H), 5.97 (d, 1H, J=4.48 Hz), 6.20 (t, 1H, J=53.72 Hz), 7.51 (d, 2H, J=8.24 Hz), 7.79 (d, 2H, J=8.28 Hz), 8.12 (d, 1H, J=8.24 Hz), 8.36-8.39 (dd, 1H, J1=2.32 Hz, J2=8.24 Hz), 8.87 (d, 1H, J=8.64 Hz), 9.03 (d, 1H, J=1.76 Hz). LC-MS (m/z): M+H=402.1.

Example 2

Preparation of 2, 2-Difluoro-N-{(1S,2R)-1-fluoromethyl-2-hydroxy-2-[4-(6-N-(cyano)methyl pyridine sulfoximine-3-yl)phenyl]-ethyl}-acetamide Scheme 2

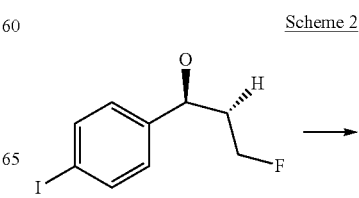

-continued

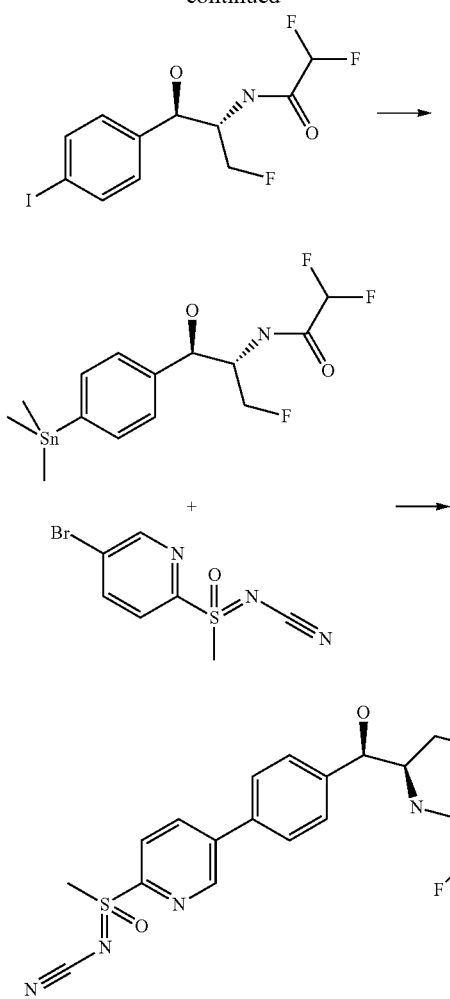

Step-1 Preparation of 2,2-difluoro-N-((1R,2S)-3-fluoro-1-hydroxy-1-(4-iodophenyl)propan-2-yl)acetamide

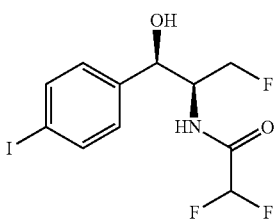 [SMILES: O=C(N[C@H](CF)[C@H](O)c1ccc(I)cc1)C(F)F]

To the solution of (1R,2S)-2-amino-3-fluoro-1-(4-iodophenyl)propan-1-ol (20.0 g, 67.8 mmol) in methanol (250 mL) is added triethylamine (15 g, 148.5 mmol) and ethyldifluoro acetate (18 g, 148.4 mmol) and reaction mixture is stirred at room temperature for 16 hours. The solvent is evaporated in vacuo and the crude material purified by column chromatography on silica gel using MeOH/DCM afford the title compound (18.3 g): 1H NMR (400 MHz, CDCl₃) 7.72 (2H, d), 7.13 (2H, d), 6.78 (1H, d), 5.85 (1H, t), 5.06 (1H, s), 4.67-4.28 (3H, m), 2.58 (1H, s).

Step-2 Preparation of 2,2-difluoro-N-((1R,2S)-3-fluoro-1-hydroxy-1-(4-(trimethylstannyl)phenyl)propan-2-yl)acetamide

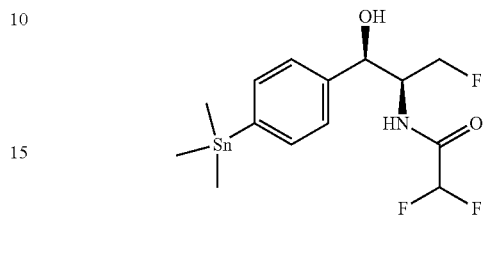

Hexamethylditin (9.9 g, 29.9 mmol) is added to a deoxygenated solution of the product of Example 17—Step 2 (10.6 g, 28.5 mmol), dichlorobis(triphenylphosphine)palladium (490 mg, 0.68 mmol) in dioxane (143 mL) and the mixture heated to 80 C for 1 hour. After cooling to r.t. the mixture is purified using column chromatography eluting from neat heptanes to neat EtOAc to give the title compound (9.3 g): 1H NMR (400 MHz, CDCl₃) 7.27 (2H, d), 7.09 (2H, d), 6.59 (1H, d), 5.62 (1H, t), 4.81-4.79 (1H, t), 4.44-4.08 (3H, m), 2.20 (1H, d), 0.14-0.00 (9H, m).

Step-3 Preparation of 2, 2-Difluoro-N-{(1S,2R)-1-fluoromethyl-2-hydroxy-2-[4-(6-N-(cyano)methyl pyridine sulfoximine-3-yl)phenyl]-ethyl}-acetamide

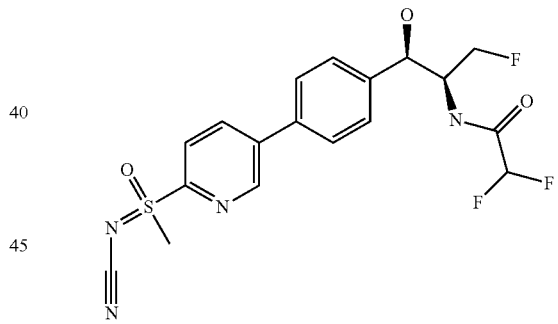

To a solution of 2,2-Difluoro-N-[(1S,2R)-1-fluoromethyl-2-hydroxy-2-(4-trimethylstannanyl-phenyl)-ethyl]-acetamide (500 mg, 1.22 mmol) in 1,4 Dioxane (10 mL) is added 5-bromo-2-N-(cyano)methyl pyridine sulfoximine (380 mg, 1.463 mmol) at room temperature. Reaction mixture is degassed with nitrogen for 10 minutes followed by addition of Pd(pph3)2.Cl2 (85 mg, 0.122 mmol) and resulting reaction mixture is heated at 50° C. for 8 h. After completion of reaction diluted with water and extracted with ethyl acetate. Organic layer is dried over sodium sulphate, evaporated in vacuo and purified by silica gel column chromatography (100-200 mesh size) using 3% methanol in DCM as an eluent to give (300 mg) as a yellow liquid compound which is repurified by preparative HPLC to afford the title compound (135 mg) as off white solid. ¹H-NMR (400 MHz, DMSO) δ: 3.77 (s, 3H), 4.32-4.35 (m, 1.5H), 4.42-4.47 (m, 0.5H), 4.56-4.57 (m, 0.5H), 4.67-4.70 (m, 0.5H), 4.93 (bs, 1H), 6.00 (bs, 1H), 6.20 (t, 1H, J=53.72 Hz), 7.54 (d, 2H, J=8.32 Hz), 7.88

(d, 2H, J=8.32 Hz), 8.28 (d, 1H, J=8.28 Hz), 8.56-8.58 (dd, 1H, J1=2.24 Hz, J2=8.32 Hz), 8.89 (d, 1H, J=8.56 Hz), 9.24 (d, 1H, J=1.84 Hz). LC-MS (m/z): M+H=427.1. HPLC=97.19%.

Example 3

Preparation of 2,2-dichloro-N-((1R,2S)-3-fluoro-1-hydroxy-1-(4-(6-(S-methylsulfonimidoyl)pyridin-3-yl)phenyl)propan-2-yl)acetamide

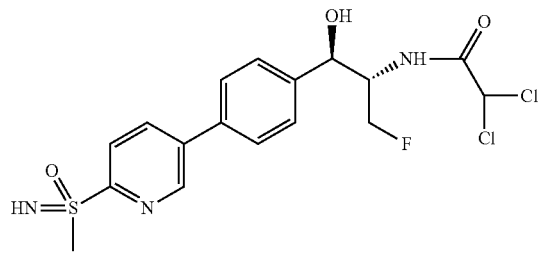 [SMILES: CS(=N)(=O)c1ccc(-c2ccc([C@@H](O)[C@@H](CF)NC(=O)C(Cl)Cl)cc2)cn1]

Step-1 Preparation of 5-{4-[(4S,5R)-3-(dichloroacetyl)-4-(fluoromethyl)-2,2-dimethyl-1,3-oxazolidin-5-yl]phenyl}-2-(S-methylsulfonimidoyl)pyridine

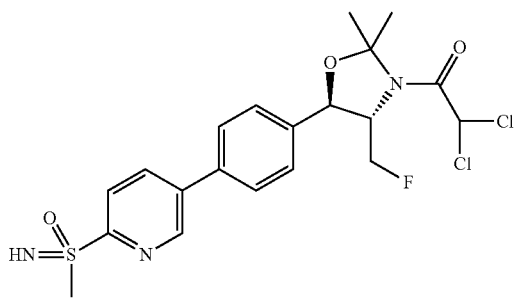 [SMILES: CC1(C)O[C@H](c2ccc(-c3ccc(S(C)(=N)=O)nc3)cc2)[C@@H](CF)N1C(=O)C(Cl)Cl]

Following the general procedure of Example 1 (Steps 1-6) and making non-critical variations but using 5-bromo-2-(S-methylsulfonimidoyl)pyridine 145 mg), the title compound is obtained (118 mg, 50%) as a tan solid, MS (ESI+) m/z 474 [M+H].

Step-2 Preparation of 2,2-dichloro-N-[(1S,2R)-1-(fluoromethyl)-2-hydroxy-2-{4-[6-(S-methylsulfonimidoyl)pyridin-3-yl]phenyl}ethyl]acetamide

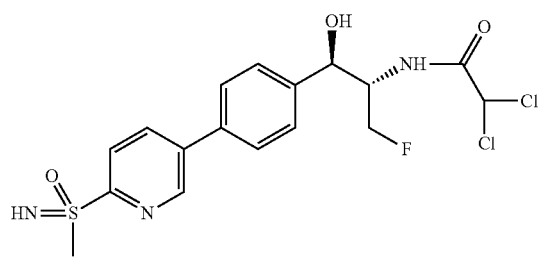 [SMILES: CS(=N)(=O)c1ccc(-c2ccc([C@@H](O)[C@@H](CF)NC(=O)C(Cl)Cl)cc2)cn1]

Following the general procedure of Example 1 (Step 7) and making non-critical variations but using 5-{4-[(4S,5R)-3-(dichloroacetyl)-4-(fluoromethyl)-2,2-dimethyl-1,3-oxazolidin-5-yl]phenyl}-2-(S-methylsulfonimidoyl)pyridine (Step 1, 115 mg) and purification by silica gel chromatography (40 g, 1-4% methanol/methylene chloride eluent), the title compound is obtained (83 mg, 79%) as a glass, $^1$H NMR (400 MHz, DMSO) δ 3.20 (s, 3H), 4.25 (m, 1.5H), 4.45 (m, 0.5H), 4.48 (m, 1H), 4.59 (m, 0.5H), 4.71 (m, 0.5H), 4.94 (m, 1H), 6.05 (d, 1H), 6.53 (s, 1H), 7.52 (d, 2H), 7.79 (d, 2H), 8.12 (d, 1H), 8.37 (dd, 1H), 8.66 (bd, 1H), 9.03 (s, 1H). MS (ESI+) m/z 434 [M+H].

Example 4

Preparation of 2, 2-Difluoro-N-{(1S,2R)-1-fluoromethyl-2-hydroxy-2-[4-(6(S-methylsulfonimidoylmethyl)pyridine-3-yl)-phenyl]-ethyl}-acetamide Scheme 3

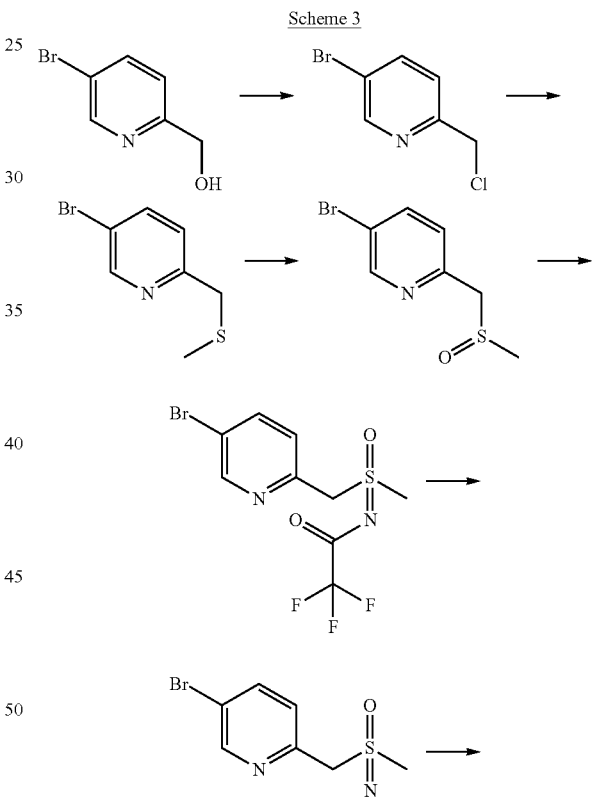

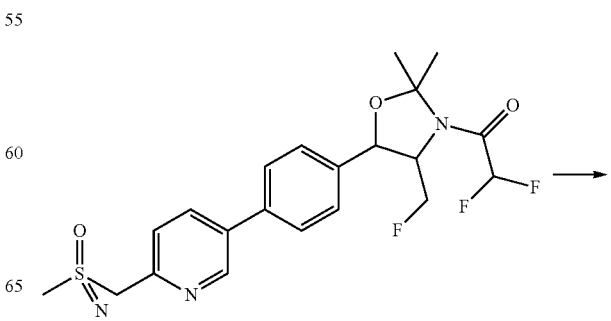

-continued

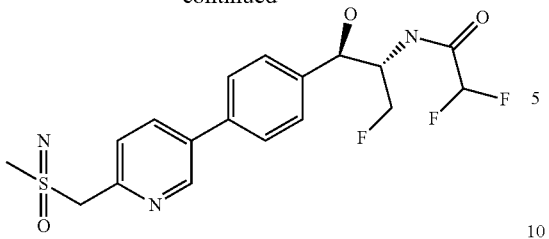

Step-1 Preparation of 5-Bromo-2-chloromethyl-pyridine

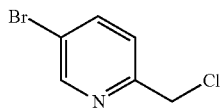

To the stirred solution of (5-Bromo-pyridin-2-yl)-Methanol (5 gm, 26.59 mmol, 1 eq) in DCM (50 mL) at 0° C. is added Thionyl chloride (3 mL) drop wise at RT then stirred at RT for 4 h. After completion, the reaction mixture quenched with saturated sodium bicarbonate solution and extracted with DCM (3×100 mL). The combined organic layer dried over sodium sulphate and evaporated under reduced pressure. The crude is purified by column chromatography using silica 100-200 mesh using 10% EtOAc: Hexane as eluent to afford title compound (4 g) as brown colored liquid. 1NMR (400 MHz, DMSO) δ: 4.77 (s, 2H), 7.54 (d, J=8.64 Hz, 1H), 8.09-8.12 (dd, J1=2.4 Hz, J2=8.32 Hz, 1H), 8.70 (d, J=5.96 Hz, 1H).

Step-2 Preparation of 5-Bromo-2-methylsulfanylmethyl-pyridine

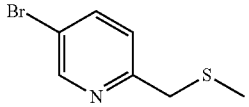

To the stirred solution of 5-Bromo-2-chloromethyl-pyridine (3.5 gm, 16.99 mmol) in DMF (25 mL) at 0° C. is added Sodium thiomethoxide (1.31 gm, 18.68 mmol) resulting reaction mixture is stirred at 0° C. for 2 h. After completion quenched with water and extracted with ethyl acetate (3×100 mL). The Combined organic layer is washed with brine and organic layer dried over sodium sulphate, evaporate under reduced pressure. The crude is purified by column chromatography using silica 100-200 mesh using 10% EtOAc: Hexane as eluent to afford title compound (3 g) as brown colored liquid. 1NMR (400 MHz, DMSO) δ: 2.00 (s, 3H), 3.75 (s, 2H), 7.39 (d, J=8.32 Hz, 1H), 7.99-8.02 (dd, J1=2.44 Hz, J2=8.32 Hz, 1H), 8.60 (d, J=2.28 Hz, 1H). LC-MS (m/z): M+H=220.1.

Step-3 Preparation of 5-Bromo-2-methanesulfinylmethyl-pyridine

To the stirred solution of 5-Bromo-2-methylsulfanylmethyl-pyridine (1.1 gm, 5.04 mmol) in MeOH: water (10:2 mL) at 0° C. is added sodium periodate (1.08 gm, 5.046 mmol) resulting reaction mixture is stirred RT for 5 h. After completion, solvent is evaporated under reduced pressure then residue is diluted with water and extract with EtOAc (3×50 mL). The combine organic layer is dried over sodium sulphate and evaporated under reduced pressure to get crude which is purified by combi flash using 8% MeOH:DCM as eluent to afford title compound (900 mg) as off white solid. 1NMR (400 MHz, DMSO) δ: 2.56 (s, 3H), 4.11 (d, J=12.6 Hz, 1H), 4.26 (d, J=12.64 Hz, 1H), 7.36 (d, J=8.28 Hz, 1H), 8.05-8.08 (dd, J1=2.44 Hz, J2=8.28 Hz, 1H), 8.71 (d, J=2.32 Hz, 1H). LC-MS (m/z): M+H=235.9.

Step-4 Preparation of 5-bromo-2-N-[(Trifluoroacetyl)methyl]-methyl pyridine sulfoximine To the stirred of 5-Bromo-2-methanesulfinylmethyl-pyridine (500 mg, 2.13 mmol) in DCM (10 mL) at 0° C. is added Triflouro acetamide (482 mg, 4.2 mmol), MgO (344 mg, 8.55 mmol) and Rh2 (OAC) 4 (28 mg, 0.64 mmol) at RT then resulting reaction mixture is stirred RT for 16 h. After completion, reaction is quenched with water and extract with EtOAc (3×25 mL). The combine organic layer is dried over sodium sulphate and evaporated under reduced pressure. The crude is purified by combi flash using 30% EtOAc: Hexane as eluent to afford title compound (300 mg) as yellow colored solid. 1NMR (400 MHz, DMSO) δ: 3.56 (s, 3H), 5.22-5.31

(m, 2H), 7.50 (d, J=8.32 Hz, 1H), 8.17-8.20 (dd, J1=2.4 Hz, J2=8.28 Hz, 1H), 8.77 (d, J=2.28, 1 H). LC-MS (m/z): M+H=245.0.

Step-5 Preparation of 5-bromo-2-(S-methylsulfonimidoylmethyl)pyridine

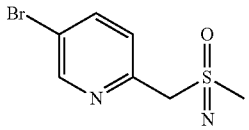

To the stirred solution of 5-bromo-2-N-[(Trifluoroacetyl)methyl]-methyl pyridine sulfoximine (300 mg, 0.87 mmol) in MeOH (2 mL) at 0° C. is added K2CO3 (600 mg, 4.38 mmol) resulting reaction mixture stirred RT for 30 min. After completion, solvent is evaporated under reduced pressure then water is added to the residue and extract with Ethyl acetate (3×25 mL). The combine organic layer is dried over sodium sulphate and evaporated under reduced pressure to afford title compound (110 mg) as yellow colored solid. 1 NMR (400 MHz, DMSO) δ: 2.87 (s, 3H), 3.80 (bs, 1H), 4.46-4.56 (m, 2H), 7.47 (d, J=8.36 Hz, 1H), 8.08-8.811 (dd, J1=2.4 Hz, J2=8.28 Hz, 1H), 8.70 (d, J=2.28 Hz, 1H). LC-MS (m/z): M+H=250.9.

Step-6 Preparation of 2, 2-Difluoro-1-{(4R,5R)-4-fluoromethyl-5-[4-(6-(S-methylsulfonimidoylmethyl)-pyridin-3-yl)-phenyl]-2,2-dimethyl-oxazolidin-3-yl}-ethanone

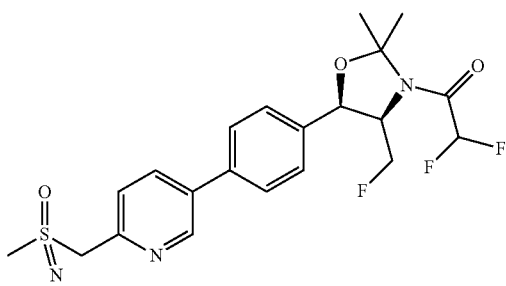 [SMILES: CC1(C)O[C@H](c2ccc(-c3ccc(CS(C)(=N)=O)nc3)cc2)[C@H](CF)N1C(=O)C(F)F]

To the degassed (30 min with nitrogen) solution of 2,2-Difluoro-1-{(4R,5R)-4-fluoromethyl-2,2-dimethyl-5-[4-(4,4,5,5-tetramethyl-[1,3,2]dioxaborolan-2-yl)-phenyl]-oxazolidin-3-yl}-ethanone (100 mg, 0.242 mmol, 1 eq), 5-bromo-2-(S-methylsulfonimidoylmethyl)pyridine (60 mg, 0.242 mmol, 1 eq) and K2CO3 (100 mg, 0.726 mmol, 3 eq) in Dioxane:water (1 mL:0.2 mL) is addition of PdCl2(dppf)2 (17 mg, 0.024 mmol, 0.1 eq) at RT. The resulting reaction is stirred at 80° C. for 16 h. After completion, reaction quenched with water and extracted with ethyl acetate (3×25 mL). The combine organic layer is dried over sodium sulphate and evaporated under reduced pressure to get crude which is purified by combi flash using 5% MeOH:DCM as eluent to afford title compound (100 mg) as sticky brown colored liquid. 1NMR (400 MHz, DMSO) δ: 1.53 (s, 3H), 1.60 (s, 3H), 2.91 (s, 3H), 3.81 (s, 1H), 3.94 (s, 1H), 4.52-4.61 (m, 2H), 4.69-4.70 (m, 1H), 4.82-4.84 (m, 0.5H), 4.91-4.95 (m, 0.5H), 5.27 (d, J=3.4 Hz, 1H), 6.64 (t, J=52.76 Hz, 1H), 7.57-7.62 (m, 3H), 7.82 (d, J=8.16 Hz, 2H), 8.14-8.16 (m, 1H), 8.91 (s, 1H). LC-MS (m/z): M+H=456.0

Step-7 Preparation of 2, 2-Difluoro-N-{(1S,2R)-1-fluoromethyl-2-hydroxy-2-[4-(6(S-methylsulfonimidoylmethyl)pyridine-3-yl)-phenyl]-ethyl}-acetamide

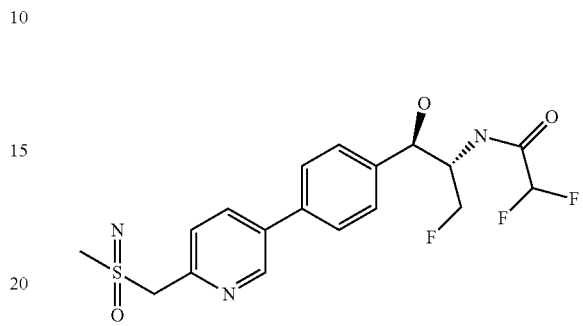

To the stirred solution of 2, 2-Difluoro-1-{(4R,5R)-4-fluoromethyl-5-[4-(6-(S-methylsulfonimidoylmethyl)-pyridin-3-yl)-phenyl]-2,2-dimethyl-oxazolidin-3-yl}-ethanone (100 mg, 0.22 mmol, 1 eq) in DCM (2 mL) at 0° C. is added TFA (1 mL) drop wise resulting reaction mixture is stirred at room temperature for 8 h. After completion, reaction solvent is evaporated under reduced pressure and residue is quenched with saturated bicarbonate solution then extracted with 10% MeOH in DCM (3×25 mL). The combined organic layer is dried over sodium sulphate and evaporated under reduced pressure. The crude is purified by combiflash using 11% MeOH in DCM as eluent to afford to title compound (23 mg) as faint brown colored solid. 1NMR (400 MHz, DMSO) δ: 2.90 (s, 3H), 3.80 (bs, 1H), 4.30-4.33 (m, 1.5H), 4.40-4.44 (m, 1H), 4.51-4.60 (m, 2H), 4.66-4.68 (m, 0.5), 4.89 (bs, 1H), 5.92 (d, J=3.96 Hz, 1H), 6.20 (t, J=53.76 Hz, 1H), 7.47 (d, J=8.24 Hz, 2H), 7.56 (d, J=8.2 Hz, 1H), 7.73 (d, J=8.32 Hz, 2H), 8.11-8.14 (dd, J1=2.4 Hz, J2=8.04 Hz, 1H), 8.85-8.89 (m, 2H). LC-MS (m/z): M+H=416.0.

Example 5

Preparation of 2, 2-Difluoro-N-{(1S,2R)-1-fluoromethyl-2-hydroxy-2-[4-(6-N-[(cyano)methyl]-methyl pyridine sulfoximine-3-yl)-phenyl]-ethyl}-acetamide Scheme 4

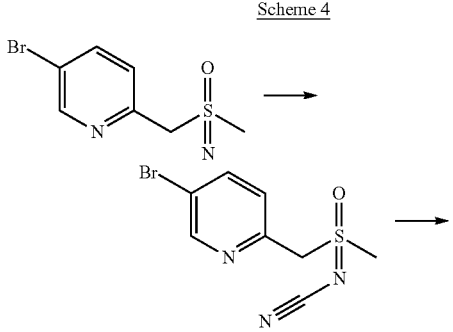

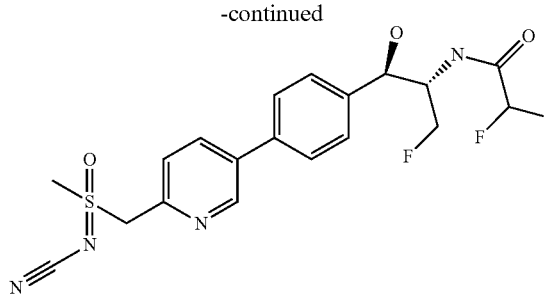

Step-1 Preparation of
5-bromo-2-N-[(cyano)methyl]-methyl pyridine
sulfoximine

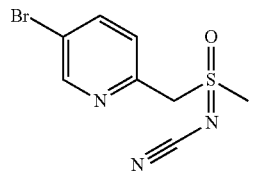

To the stirred solution of 5-bromo-2-(S-methylsulfonimidoylmethyl)pyridine (150 mg, 0.602 mmol, 1 eq) in DCM (2 mL) at 0° C. is added DMAP (0.081 mg, 0.663 mmol, 1.1 eq) and cyanogen bromide (127 mg, 1.20 mmol, 2 eq) at RT then stirred for 16 h at same temperature. After completion, reaction quenched with water then aqueous extracted with DCM (3×25 mL). The combined organic layer is dried over sodium sulphate and evaporated under reduced pressure. The crude is purified by column chromatography using 35% EtOAc:Hexane as eluent to afford title compound (90 mg) as yellow colored solid. 1NMR (400 MHz, CDCl$_3$) δ: 3.23 (s, 3H), 4.68-4.77 (m, 2H), 7.46 (d, J=8.24 Hz, 1H), 7.94-7.97 (dd, J1=2.24 Hz, J2=8.24 Hz, 1H), 8.69 (d, J=2.08 Hz, 1H). LC-MS (m/z): M+H=274.9.

Step-2 Preparation of 2, 2-Difluoro-N-{(1S,2R)-1-fluoromethyl-2-hydroxy-2-[4-(6-N-[(cyano)methyl]-methyl pyridine sulfoximine-3-yl)-phenyl]-ethyl}-acetamide

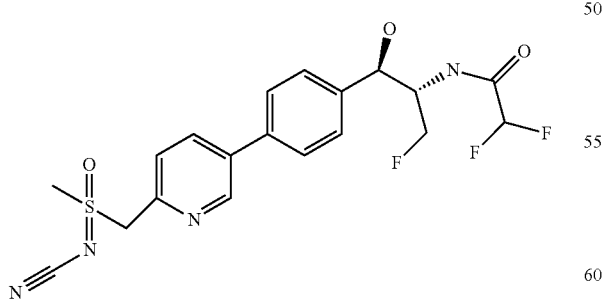

To the degassed (30 min by nitrogen) solution of 2,2-Difluoro-N-[(1S,2R)-1-fluoromethyl-2-hydroxy-2-(4-trimethylstannanyl-phenyl)-ethyl]-acetamide (130 mg, 0.317 mmol, 1 eq), 5-bromo-2-N-[(cyano)methyl]-methyl pyridine sulfoximine (86 mg, 0.317 mmol, 1 eq) in NMP (3 mL) is added of Pd2(dba)3 (29 mg, 0.032 mmol, 0.1 eq), Tri-2-furylphosphine (14 mg, 0.063 mmol, 0.2 eq) at RT. The resulting reaction is stirred at 60° C. for 16 h. After completion, reaction is quenched with water and extract with ethyl acetate (3×25 mL). The combined organic layer washed with brine solution, dried over sodium sulphate and evaporated under reduced pressure. The crude is purified by combi flash using 7% MeOH:DCM as eluent to afford (32 mg) as colorless gummy compound which is repurified by prepTLC using 5% MeOH:DCM to afford the title compound (15 mg) as off-white solid. 1NMR (400 MHz, DMSO) δ: 3.52 (s, 3H), 4.30 (m, 1.5H), 4.41-4.43 (m, 0.5H), 4.55 (m, 0.5H), 4.67 (m, 0.5H), 4.90 (s, 1H), 5.24 (s, 2H), 5.94 (s, 1H), 6.20 (t, J=53.92 Hz, 1H), 7.48 (d, J=7.84 Hz, 2H), 7.67 (d, J=7.8 Hz, 1H), 7.76 (d, J=7.8 Hz, 2H), 8.22 (d, J=8.16 Hz, 1H), 8.85 (d, J=8.04 Hz, 1H), 8.97 (s, 1H). LC-MS (m/z): M−H=439.2.

Example 6

Preparation of 2,2-dichloro-N-((1R,2S)-3-fluoro-1-hydroxy-1-(4-(S-methylsulfonimidoyl)phenyl) propan-2-yl)acetamide Scheme 5

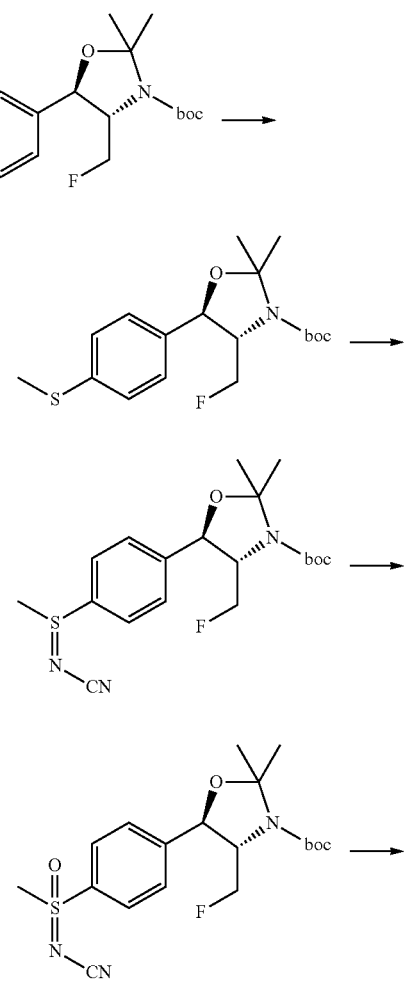

-continued

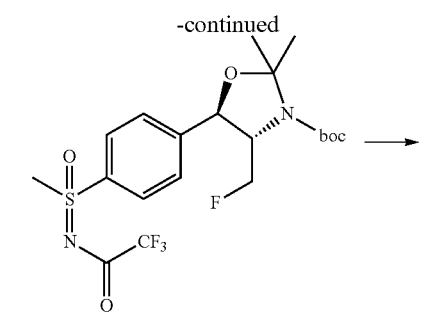

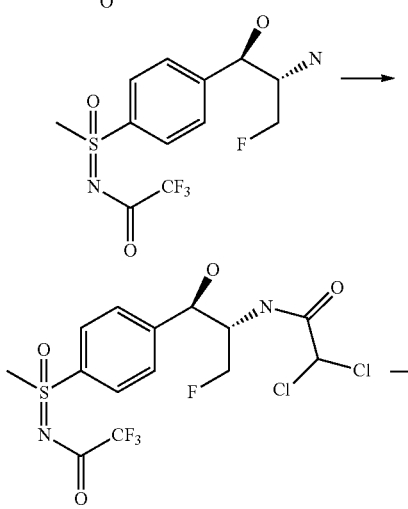

Step-1 Preparation of (4S,5R)-tert-butyl 4-(fluoromethyl)-2,2-dimethyl-5-(4-(methyl thio) phenyl) oxazolidine-3-carboxylate

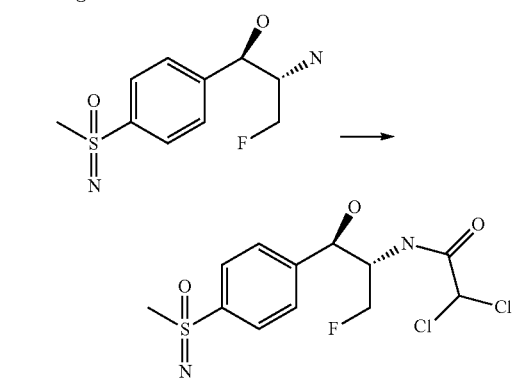

To a solution of (4S,5R)-4-Fluoromethyl-5-(4-iodo-phenyl)-2,2-dimethyl-oxazolidine-3-carboxylic acid tert-butyl ester (4.6 g, 10.575 mmol) in DMSO (50 mL) is added Sodium thiomethoxide (0.88 g, 12.69 mmol), CuI (0.201 g, 1.057 mmol) and L-proline sodium salt (0.29 g, 2.115 mmol) and heated the mixture at 90° C. for 48 h. Reaction mixture is quenched with water and extracted with ethyl acetate. Organic layer is washed with brine and dried over sodium sulphate, concentrated and purified by column chromatography using silica (100-200) mesh size using 3% ethyl acetate in hexane as an eluent to afford title compound (1.7 g) as faint yellow oil. $^1$H-NMR (400 MHz, DMSO): δ 1.42 (s, 9H), 1.47 (s, 3H), 1.59 (s, 3H), 2.47 (s, 3H), 3.73-3.79 (m, 1H), 4.37-4.92 (m, 1H), 4.71-4.94 (m, 1H), 5.01 (d, J=7.44 Hz, 1H), 7.27 (d, J=8.28 Hz, 2H), 7.39 (d, J=8.36 Hz, 2H). LC-MS (m/z): M+H=356.2.

Step-2 Preparation of (4S,5R)-tert-butyl 4-(fluoromethyl)-2,2-dimethyl-5-(4-(S-(cyano)methyl sulfinimidoyl) phenyl) oxazolidine-3-carboxylate

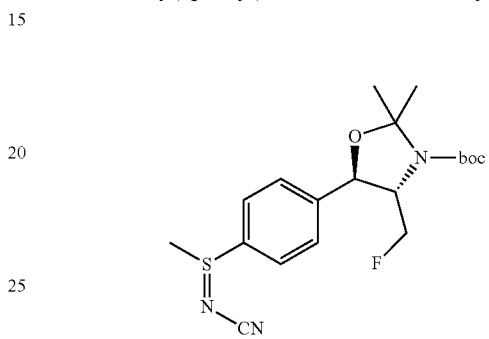

To a solution of (4S,5R)-tert-butyl 4-(fluoromethyl)-2,2-dimethyl-5-(4-(methyl thio)phenyl) oxazolidine-3-carboxylate (1.6 g, 4.507 mmol) in methanol (75 mL) is added NH2CN (50% aqueous solution) (0.27 g, 5.859 mmol) and t-BuOK (0.606 g, 5.408 mmol) at 0° C. followed by addition of NBS (1.203 g, 6.761 mmol) is added and resulting reaction mixture is stirred at RT for 1 h. Solvent is evaporated in vacuo; reaction mixture is quenched with aqueous sodium metabisulphate solution and extracted with ethyl acetate. Organic layer is dried over sodium sulphate, concentrated and purified by combi-flash chromatography using 10% methanol in DCM as an eluent to afford title compound (1.7 g) as colorless oil. $^1$H-NMR (400 MHz, DMSO): δ 1.42 (s, 9H), 1.50 (s, 3H), 1.62 (s, 3H), 3.16 (s, 3H), 3.88-3.94 (m, 1H), 4.51-4.61 (m, 1H), 4.80 (m, 1H), 5.19 (d, J=7.08 Hz, 1H), 7.77 (d, J=8.36 Hz, 2H), 7.92 (d, J=8.24 Hz, 2H). LC-MS (m/z): M+H=394.2.

Step-3 Preparation of (4S,5R)-tert-butyl 4-(fluoromethyl)-2,2-dimethyl-5-(4-(S-(cyano)methyl sulfoximine) phenyl) oxazolidine-3-carboxylate

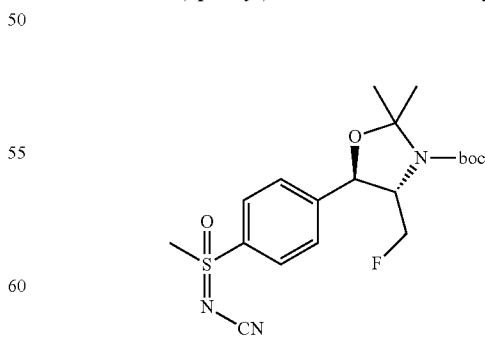

To a solution of (4S,5R)-tert-butyl 4-(fluoromethyl)-2,2-dimethyl-5-(4-(S-(cyano)methyl sulfinimidoyl)phenyl) oxazolidine-3-carboxylate (1.6 g, 4.051 mmol) in ethanol (580 mL) is added K$_2$CO$_3$ (1.677 g, 12.152 mmol) at 0° C.

followed by addition of m-CPBA (1.014 g, 6.076 mmol) at 0° C. The resulting reaction mixture is stirred at 0° C. for 10 h. Solvent is evaporated in vacuo, reaction mixture is quenched with water and extracted with DCM. Organic layer is dried over sodium sulphate, concentrated and purified by combi-flash chromatography using 30% ethyl acetate in n-Hexane as an eluent to afford title compound (1 g) yellow oil. LC-MS (m/z): M+H=412.0.

Step-4 Preparation of (4S,5R)-tert-butyl 4-(fluoromethyl)-2,2-dimethyl-5-(4-(S-methyl-N-(2,2,2-trifluoroacetyl)sulfonimidoyl)phenyl)oxazolidine-3-carboxylate

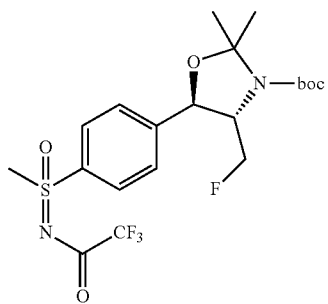

To a solution of (4S,5R)-tert-butyl 4-(fluoromethyl)-2,2-dimethyl-5-(4-(S-(cyano)methyl sulfoximine)phenyl)oxazolidine-3-carboxylate (930 mg, 2.263 mmol) in DCM (20 mL) is added Trifluoroacetic anhydride (1.42 mL). Reaction mixture is allowed to stir at room temperature for 16 h. Excess of Trifluoroacetic acid and DCM is evaporated in vacuo, stripped with toluene followed by washing with n-pentane and diethyl ether to afford title compound (500 mg, crude) as faint yellow sticky mass which is used as such for next step.

Step-5 Preparation of (1R,2S)-2-Amino-3-fluoro-1-(4-(methyl-N-(2,2,2-trifluoroacetyl)sulfonimidoyl)phenyl)-propan-1-ol

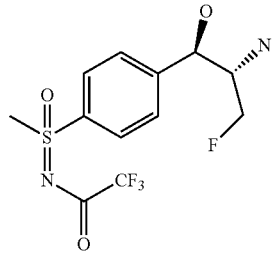 [SMILES: CS(=O)(=NC(=O)C(F)(F)F)c1ccc([C@@H](O)[C@H](N)CF)cc1]

To a solution of (4S,5R)-tert-butyl 4-(fluoromethyl)-2,2-dimethyl-5-(4-(methyl-N-(2,2,2-trifluoroacetyl)sulfonimidoyl)phenyl)oxazolidine-3-carboxylate (500 mg, 1.168 mmol) in DCM (20 mL) is added Trifluoroacetic acid (2.0 mL). Reaction mixture is allowed to stir at room temperature for 2 h. Excess of Trifluoroacetic acid and DCM is evaporated in vacuo, stripped with toluene followed by washing with n-pentane and diethyl ether to afford crude title compound (426 mg, TFA salt) as faint yellow sticky mass which is used as such for next step.

Step-6 Preparation of 2, 2-Dichloro-N-[(1S,2R)-1-fluoromethyl-2-hydroxy-2-(4-(methyl-N-(2,2,2-trifluoroacetyl)sulfonimidoyl)phenyl)-ethyl]-acetamide

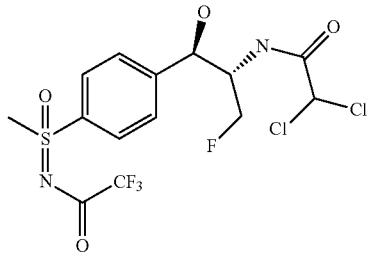 [SMILES: CS(=O)(=NC(=O)C(F)(F)F)c1ccc([C@@H](O)[C@@H](CF)NC(=O)C(Cl)Cl)cc1]

To a solution of (1R,2S)-2-Amino-3-fluoro-1-(4-(methyl-N-(2,2,2-trifluoroacetyl)sulfonimidoyl)phenyl)-propan-1-ol TFA salt (426 mg, 1.479 mmol) in Methanol (5 mL) is added TEA (0.299 mL, 2.95 mmol) followed by addition of ethyl-dichloroacetate (0.279 mL, 1.775 mmol) The resulting reaction mixture is stirred at room temperature for 16 h. Solvent is evaporated in vacuo to get crude which is purified by combi-flash chromatography using 10.3% MeOH in DCM as an eluent to afford title compound (212 mg) as yellow oil. $^1$H-NMR (400 MHz, DMSO) δ: 3.02 (s, 3H), 4.19-4.13 (m, 1H), 4.15 (bs, 1H), 4.36-4.41 (m, 1.5H), 4.44-4.56 (m, 1H), 4.66-4.69 (m, 0.5H), 4.93 (t, J=4.56 Hz, 1H), 6.0 (d, J=4.64 Hz, 1H), 7.54 (d, J=8.28 Hz, 2H), 7.87 (d, J=8.36 Hz, 2H), 9.49 (d, J=8.36 Hz, 1H). LC-MS (m/z): M+H=343.1 (fragment).

Step-7 Preparation of (1R,2S)-2-amino-3-fluoro-1-(4-(S-methylsulfonimidoyl)phenyl) propan-1-ol

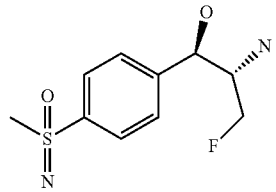 [SMILES: CS(=N)(=O)c1ccc([C@@H](O)[C@H](N)CF)cc1]

To a solution of 2, 2-Dichloro-N-[(1S,2R)-1-fluoromethyl-2-hydroxy-2-(4-(methyl-N-(2,2,2-trifluoroacetyl)sulfonimidoyl)phenyl)-ethyl]-acetamide (212 mg, 0.468 mmol) in Methanol (20 mL) is added K2CO3 (322.9 mg, 2.34 mmol) the resulting reaction mixture is stirred at room temperature for 16 h. Solvent is evaporated in vacuo to get crude which is purified by combi-flash chromatography using 15% MeOH in DCM as an eluent and washed with n-pentane and diethyl ether to afford title compound (80 mg). $^1$H-NMR (400 MHz, DMSO) δ: 1.60 (bs, 2H), 3.04 (s, 3H), 4.13-4.15 (m, 1.5H), 4.21-4.42 (m, 0.5H), 4.42-4.31 (m, 0.5H), 4.39-4.43 (m, 0.5H), 4.66 (bs, 1H), 7.55 (d, J=8.28 Hz, 2H), 7.87 (d, J=8.32 Hz, 2H). LC-MS (m/z): M+H=247.2.

Step-8 Preparation of 2,2-dichloro-N-((1R,2S)-3-fluoro-1-hydroxy-1-(4-(S-methylsulfonimidoyl)phenyl)propan-2-yl)acetamide

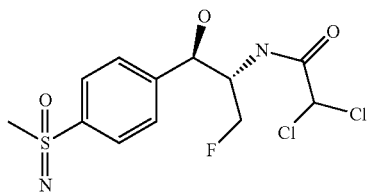 [SMILES: CS(=N)(=O)c1ccc([C@@H](O)[C@@H](CF)NC(=O)C(Cl)Cl)cc1]

To a solution of (1R,2S)-2-amino-3-fluoro-1-(4-(S-methylsulfonimidoyl)phenyl)propan-1-ol (76 mg, 0.308 mmol) Methanol (5 mL) is added TEA (0.047 mL, 0.462 mmol) followed by addition of ethyldichloroacetate (0.048 mL, 0.308 mmol) The resulting reaction mixture is stirred at room temperature for 16 h. Solvent is evaporated in vacuo to get crude which is purified by combi-flash chromatography using 0.6% MeOH in DCM as an eluent to get 40 mg of the compound which is re-purified by prep HPLC to afford title compound (25 mg) white solid. $^1$H-NMR (400 MHz, DMSO) δ: 3.0 (s, 3H), 4.19-4.25 (m, 2H), 4.28-4.32 (m, 0.5H), 4.40-4.44 (m, 0.5H), 4.56-4.59 (m, 0.5H), 4.67-4.71 (m, 0.5H), 4.96 (bs, 1H), 6.12 (d, 1H, J=3.6 Hz), 6.47 (d, 1H, J=1.88 Hz), 7.56 (d, 2H, J=8.28 Hz), 7.54 (d, 2H, J=8.28 Hz), 8.82 (d, 1H, J=8.28 Hz). LC-MS (m/z): M+H=357.0.

Example 7

Preparation of 2, 2-Dichloro-N-[(1S,2R)-1-fluoromethyl-2-hydroxy-2-(4-(cyano)-methyl-phenyl sulfoximine)-ethyl]-acetamide Scheme 6

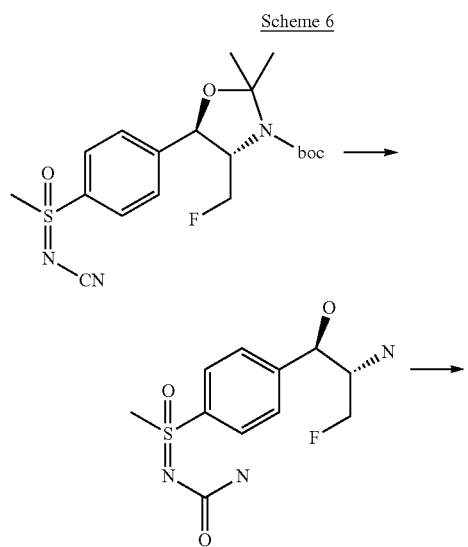

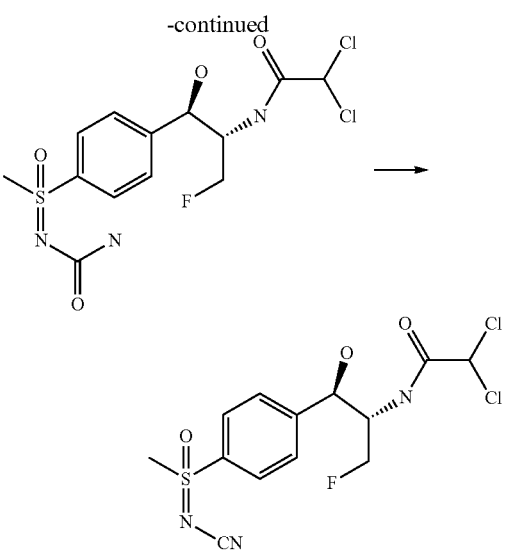

Step-1 Preparation of (1R,2S)-2-Amino-3-fluoro-1-(4-(N-carbamoyl-S-methylsulfonimidoyl)phenyl)-propan-1-ol

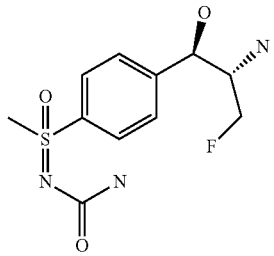 [SMILES: CS(=O)(=NC(N)=O)c1ccc([C@@H](O)[C@H](N)CF)cc1]

To a solution of (4S,5R)-tert-butyl 4-(fluoromethyl)-2,2-dimethyl-5-(4-(S-(cyano)methyl sulfoximine)phenyl) oxazolidine-3-carboxylate (290 mg, 0.706 mmol) in DCM (5 mL) is added Trifluoroacetic anhydride (1.16 mL) at 0° C. and stirred at 0° C. for 6 h. After completion of reaction, excess of Triflouroacetic acid and DCM is evaporated in vacuo, stripped with toluene followed by washing with n-pentane and diethyl ether to afford title compound (250 mg, TFA salt) as off white solid. LC-MS (m/z): M+H=290.2.

Step-2 Preparation of N-((1R,2S)-1-(4-(N-carbamoyl-S-methylsulfonimidoyl)phenyl)-3-fluoro-1-hydroxypropan-2-yl)-2,2-dichloroacetamide

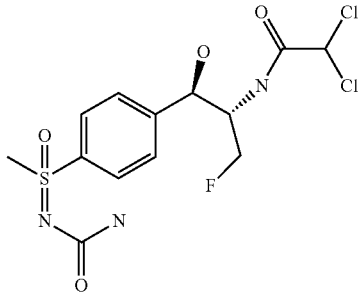 [SMILES: CS(=O)(=NC(N)=O)c1ccc([C@@H](O)[C@@H](CF)NC(=O)C(Cl)Cl)cc1]

To a solution of (1R,2S)-2-Amino-3-fluoro-1-(4-(N-carbamoyl-S-methylsulfonimidoyl)phenyl)-propan-1-ol TFA salt (250 mg, 0.865 mmol) in Methanol (5 mL) is added TEA (0.175 mL, 1.73 mmol) followed by addition of ethyldichloroacetate (128.72 mL, 1.038 mmol) at room temperature. The resulting reaction mixture is stirred at room temperature for 16 h. Solvent is evaporated in vacuo and obtained crude is purified by combi-flash chromatography using 6% MeOH in DCM as an eluent to give 200 mg of title compound as off white solid. ¹H-NMR (400 MHz, DMSO): δ 2.99 (s, 3H), 4.25-4.32 (m, 1.5H), 4.40-4.44 (m, 0.5H), 4.56-4.59 (m, 0.5H), 4.67-4.71 (m, 0.5H), 4.97 (bs, 1H), 6.05 (bs, 1H), 6.18 (m, 1H), 6.46-6.48 (m, 1H), 7.61 (d, J=7.52 Hz, 2H), 7.86 (d, J=8 Hz, 2H), 8.63-8.67 (m, 2H). LC-MS (m/z): M+H=399.8.

Step-3 Preparation of 2, 2-Dichloro-N-[(1S,2R)-1-fluoromethyl-2-hydroxy-2-(4-(cyano)-methyl-phenyl sulfoximine)-ethyl]-acetamide

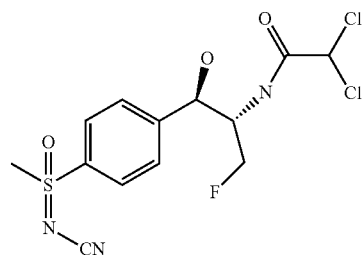 [SMILES: CS(=O)(=NC#N)c1ccc([C@@H](O)[C@@H](CF)NC(=O)C(Cl)Cl)cc1]

To a solution of N-((1R,2S)-1-(4-(N-carbamoyl-S-methyl-sulfonimidoyl)phenyl)-3-fluoro-1-hydroxypropan-2-yl)-2,2-dichloroacetamide (200 mg, 0.501 mmol) in THF (2 mL) is added Triflouroacetic anhydride (0.084 mL, 0.602 mmol) at 0° C. After 5 minutes stirring TEA (101 mg, 1.003 mmol) is added. The resulting reaction mixture is stirred at room temperature for 24 h then at 50° C. for 16 h. Solvent is evaporated in vacuo and obtained crude is purified by prep HPLC to give 5 mg of title compound and 25 mg of the compound. Analytical data for 43732-315082: ¹H-NMR (400 MHz, DMSO): δ 3.31 (s, 3H), 4.34-4.37 (m, 1H), 4.48-4.51 (m, 0.5H), 4.56-4.62 (m, 1H), 4.63-4.69 (m, 0.5H), 5.23 (bs, 1H), 5.81 (d, 1H, J=3.04 Hz), 7.01 (d, J=6.24 Hz, 1H), 7.69 (d, J=8.32 Hz, 2H), 7.94 (d, J=7.84 Hz, 2H). LC-MS (m/z): M+H=382.0.

Example 8

Preparation of 2, 2-Difluoro-N-[(1S,2R)-1-fluoromethyl-2-hydroxy-2-(4-(cyano)-methyl-phenyl sulfoximine)-ethyl]-acetamide Scheme 7

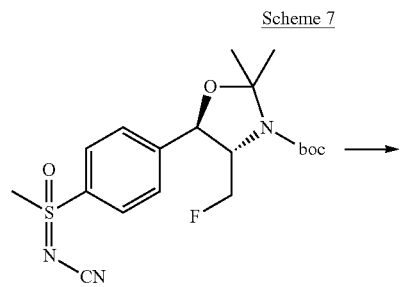

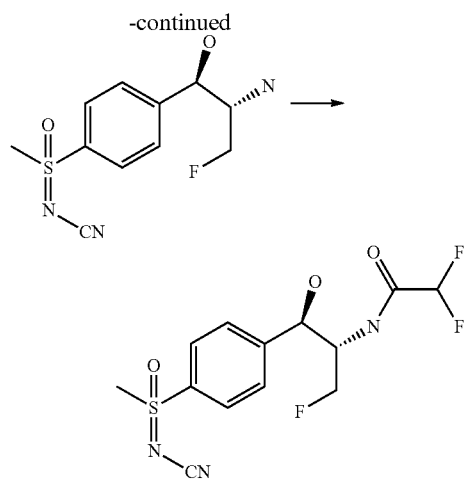

Step-1 Preparation of (1R,2S)-2-Amino-3-fluoro-1-(4-(cyano)-methyl sulfoximine-phenyl)-propan-1-ol

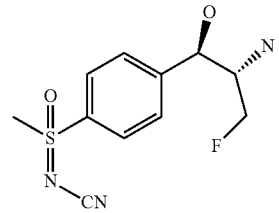 [SMILES: CS(=O)(=NC#N)c1ccc([C@@H](O)[C@H](N)CF)cc1]

To a solution of (4S,5R)-tert-butyl 4-(fluoromethyl)-2,2-dimethyl-5-(4-(S-(cyano)methyl sulfoximine)phenyl) oxazolidine-3-carboxylate (200 mg, 0.487 mmol) in DCM (10 mL) is added Trifluoroacetic acid (0.8 mL). Reaction mixture is allowed to stir at room temperature for 2 h. Excess of Trifluoroacetic acid and DCM is evaporated in vacuo, stripped with toluene followed by washing with n-pentane and diethyl ether to afford title compound (121 mg, TFA salt) as faint yellow sticky mass. LC-MS (m/z): M+H=272.0.

Step-2 Preparation of 2, 2-Difluoro-N-[(1S,2R)-1-fluoromethyl-2-hydroxy-2-(4-(cyano)-methyl-phenyl sulfoximine)-ethyl]-acetamide

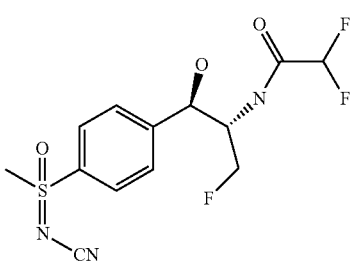 [SMILES: CS(=O)(=NC#N)c1ccc([C@@H](O)[C@@H](CF)NC(=O)C(F)F)cc1]

To a solution of (1R,2S)-2-Amino-3-fluoro-1-(4-(cyano)-methyl sulfoximine-phenyl)-propan-1-ol TFA salt (121 mg, 0.294 mmol) in Methanol (5 mL) is added TEA (1167 mg, 0.05 mL, 0.589 mmol) followed by addition of ethyldifluoroacetate (0.044 mL, 0.353 mmol) The resulting reaction mixture is stirred at room temperature for 16 h. Solvent is evaporated in vacuo to get crude which is purified by combiflash chromatography using 6% MeOH in DCM as an eluent to afford 40 mg of the compound which is repurified by prep HPLC to afford title compound (13 mg) as white sticky mass. ¹H-NMR (400 MHz, DMSO) δ: 3.70 (s, 3H), 4.31-4.38 (m, 1.5H), 4.43-4.47 (m, 0.5H), 4.57-4.58 (m, 0.5H), 4.67-4.69 (m, 0.5H), 5.00 (d, J=2.92 Hz, 1H), 6.16 (t, J=53.72 Hz, 1H), 6.21 (bs, 1H), 7.74 (d, J=7.72 Hz, 2H), 8.0 (d, J=8.4 Hz. 2H,), 8.91 (d, J=7.12 Hz, 1H). LC-MS (m/z): M+H=348.2.

Example 9

Preparation of 2,2-dichloro-N-((1R,2S)-3-fluoro-1-(4-(S-(fluoromethyl)sulfonimidoyl)phenyl)-1-hydroxypropan-2-yl)

Scheme 8

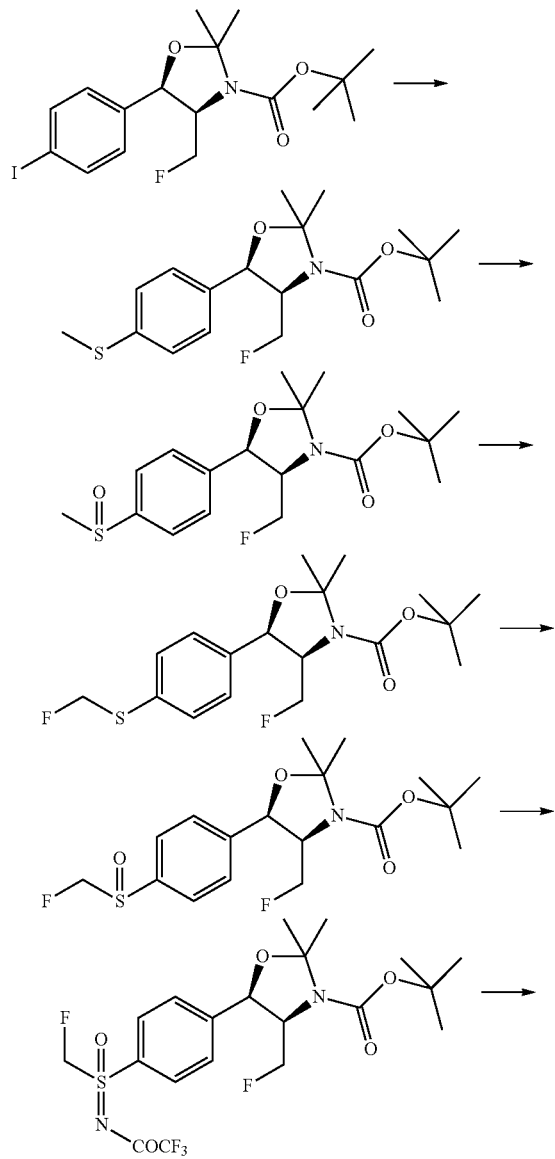

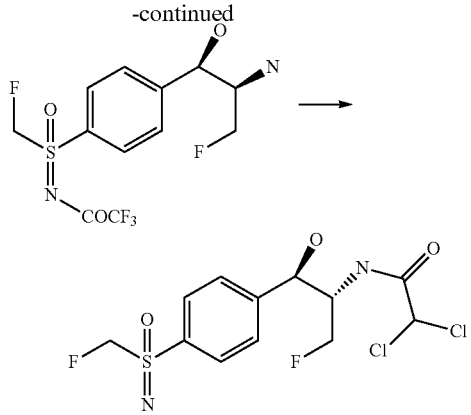

Step-1 Preparation of (4R,5R)-4-Fluoromethyl-2,2-dimethyl-5-(4-methylsulfanyl-phenyl)-oxazolidine-3-carboxylic acid tert-butyl ester

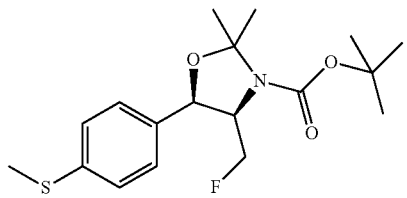 [SMILES: CSc1ccc([C@H]2OC(C)(C)N(C(=O)OC(C)(C)C)[C@H]2CF)cc1]

To a solution of (4R,5R)-4-Fluoromethyl-5-(4-iodo-phenyl)-2,2-dimethyl-oxazolidine-3-carboxylic acid tert-butyl ester (2.4 g, 5.51 mmol) in DMSO (40 mL) is added Sodium thiomethoxide (0.463 g, 6.621 mmol), CuI (0.105 g, 0.552 mmol) and L-proline sodium salt (0.151 g, 1.103 mmol) and heated the mixture at 90° C. for 24 h. Reaction mixture is quenched with water and extracted with ethyl acetate. Organic layer is washed with brine and dried over sodium sulphate, concentrated and purified by CombiFlash using 120 g column with 9.26% ethyl acetate in hexane as an eluent to afford title compound (1.7 g) as faint yellow solid. ¹H-NMR (400 MHz, DMSO): δ 1.42 (s, 9H), 1.47 (s, 3H), 1.59 (s, 3H), 2.47 (s, 3H), 3.73-3.79 (m, 1H), 4.37-4.92 (m, 1H), 4.71-4.94 (m, 1H), 5.01 (d, J=7.44 Hz, 1H), 7.27 (d, J=8.28 Hz, 2H), 7.39 (d, J=8.36 Hz, 2H). LC-MS (m/z): M+H=356.2.

Step-2 Preparation of (4R,5R)-4-Fluoromethyl-5-(4-methanesulfinyl-phenyl)-2,2-dimethyl-oxazolidine-3-carboxylic acid tert-butyl ester

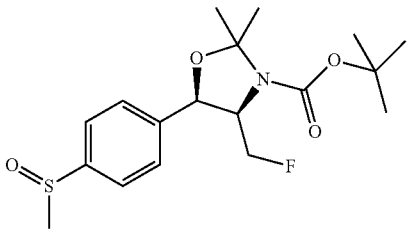 [SMILES: CS(=O)c1ccc([C@H]2OC(C)(C)N(C(=O)OC(C)(C)C)[C@H]2CF)cc1]

To a solution of (4R,5R)-4-Fluoromethyl-2,2-dimethyl-5-(4-methylsulfanyl-phenyl)-oxazolidine-3-carboxylic acid tert-butyl ester (6 g, 16.91 mmol) in ethanol (300 mL) is cooled to 0° C. followed by addition of K2CO3 (4.665 g, 33.80 mmol) and m-CPBA (2.90, 16.90 mmol) at 0° C. and resulting reaction mixture is stirred at 0° C. for 10 h. After completion, reaction mixture is quenched with water and extracted with ethyl acetate. Organic layer is dried over sodium sulphate, concentrated and purified by CombiFlash using 120 g column with 100% ethyl acetate in hexane as an eluent to afford title compound (4 g) as colorless oil. $^{1}$H-NMR (400 MHz, DMSO): δ 1.43 (s, 9H), 1.50 (s, 3H), 1.62 (s, 3H), 2.74 (s, 3H), 3.82-3.89 (m, 1H), 4.46-4.57 (m, 1H), 4.81 (m, 1H), 5.15 (d, J=7.28 Hz, 1H), 7.65-7.72 (m, 4H). LC-MS (m/z): M+H=372.3.

Step-3 Preparation of (4R,5R)-4-Fluoromethyl-5-(4-fluoromethylsulfanyl-phenyl)-2,2-dimethyl-oxazolidine-3-carboxylic acid tert-butyl ester

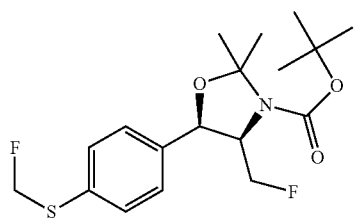 [SMILES: CC(C)(C)OC(=O)N1[C@@H](CF)[C@@H](c2ccc(SCF)cc2)OC1(C)C]

To a solution of (4R,5R)-4-Fluoromethyl-5-(4-methanesulfinyl-phenyl)-2,2-dimethyl-oxazolidine-3-carboxylic acid tert-butyl ester (1.0 g, 2.69 mmol) in DCM (50 mL) is cooled to 0° C. followed by addition of SbCl3 (0.018 g, 0.081 mmol) and DAST (0.6 mL, 4.582 mmol). The resulting reaction mixture is stirred at RT for 16 h. After completion reaction mixture is quenched with aqueous bicarbonate solution and extracted with ethyl acetate. Organic layer is dried over sodium sulphate, concentrated and purified by combi-flash chromatography (12 g column) using 8% ethyl acetate in n-Hexane as an eluent to afford title compound (564 mg) as colorless oil. $^{1}$H-NMR (400 MHz, DMSO): δ 1.41 (s, 9H), 1.48 (s, 3H), 1.61 (s, 3H), 377-.382 (m, 1H), 4.42-4.53 (m, 1H), 4.76-4.92 (m, 1H), 5.06 (d, J=7.36 Hz, 1H), 5.99 (d, J=52.32 Hz, 2H), 7.46-7.51 (m, 4H). LC-MS (m/z): M+H=374.1.

Step-4 Preparation of (4R,5R)-5-(4-Fluoromethanesulfinyl-phenyl)-4-fluoromethyl-2,2-dimethyl-oxazolidine-3-carboxylic acid tert-butyl ester

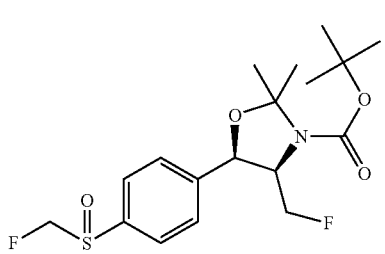 [SMILES: CC(C)(C)OC(=O)N1[C@@H](CF)[C@@H](c2ccc(S(=O)CF)cc2)OC1(C)C]

To a solution of (4R,5R)-4-Fluoromethyl-5-(4-fluoromethylsulfanyl-phenyl)-2,2-dimethyl-oxazolidine-3-carboxylic acid tert-butyl ester (2.67 g, 7.158 mmol) in DCM (250 mL) is cooled to −78° C. followed by addition of solution of m-CPBA (1.59 g, 7.158 mmol) in DCM (25 mL). Reaction mixture is allowed to stir −78° C. for 20 minutes. After completion of the reaction mixture is quenched with aqueous bicarbonate solution and extracted with DCM. Organic layer is dried over sodium sulphate, concentrated and purified by combi-flash chromatography (40 g column) using 78% ethyl acetate in hexane as an eluent to afford title compound (1.88 g) as colorless oil. $^{1}$H-NMR (400 MHz, DMSO): δ 1.42 (s, 9H), 1.50 (s, 3H), 1.62 (s, 3H), 383-.388 (m, 1H), 4.46-4.58 (m, 1.5H), 4.75-4.84 (m, 1.5H), 5.17 (d, J=7.2 Hz, 1H), 5.25-5.27 (dd, J=1.12 Hz, J=8.8 Hz, 0.5H), 5.37-5.39 (m, 0.5H), 5.51-5.54 (dd, J=2.44 Hz, J=8.84 Hz, 0.5H), 5.63-5.64 (m, 0.5H), 7.70-7.77 (m, 4H). LC-MS (m/z): M+H=390.4.

Step-5 Preparation of (4R,5R)-5-(N-[(Trifluoroacetyl)methyl phenyl sulfoximine)-4-fluoromethyl-2,2-dimethyl-oxazolidine-3-carboxylic acid tert-butyl ester

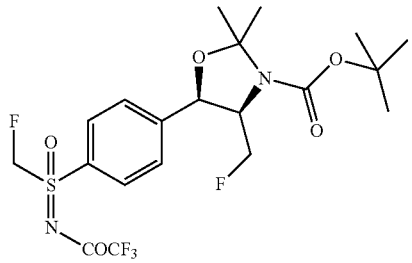

To the stirred of (4R,5R)-5-(4-Fluoromethanesulfinyl-phenyl)-4-fluoromethyl-2,2-dimethyl-oxazolidine-3-carboxylic acid tert-butyl ester (1.88 g, 4.833 mmol) in DCM (140 mL) is added Trifluoro acetamide (1.092 g, 9.66 mmol), PhI(OAc)2(2.33 g, 7.249 mmol) and MgO (0.779 g, 19.332 mmol) and resulting reaction mixture is degassed with nitrogen for 15 minutes followed by addition of Rh2(OAC)4 (0.534 g, 1.208 mmol) resulting reaction mixture is stirred RT for 16 h. After completion reaction mixture is quenched with water and extract with DCM combine organic layer is dried over sodium sulphate and evaporated under reduced pressure to get crude which is purified by combi flash (40 g column) and compound is eluted with 55% EtOAc:Hexane to afford title compound (1.46 g) as colorless oil. 1NMR (400 MHz, DMSO) δ: 1.42 (s, 9H), 1.51 (s, 3H), 1.63 (s, 3H), 3.91-3.97 (m, 1H), 4.55-4.67 (m, 1.5H), 4.77-4.90 (m, 1.5H), 5.28 (d, J=6.92 Hz, 1H), 6.22-6.40 (m, 2H), 7.91 (d, J=8.52 Hz, 2H), 8.05 (d, J=8.52 Hz, 2H). LC-MS (m/z): M+H=499.1.

Step-6 Preparation of (1R,2S)-2-Amino-3-fluoro-1-(N-[(Trifluoroacetyl)methyl phenyl sulfoximine)-propan-1-ol

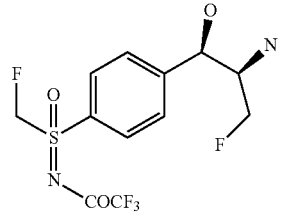

To a solution of (4R,5R)-5-(N-[(Trifluoroacetyl)methyl phenyl sulfoximine)-4-fluoromethyl-2,2-dimethyl-oxazolidine-3-carboxylic acid tert-butyl ester (1.46 g, 5.489 mmol) in DCM (30 mL) is added Trifluoroacetic acid (3 mL). Reaction mixture is allowed to stir at room temperature for 4 h. Excess of Trifluoroacetic acid and DCM is evaporated in vacuo, stripped with DCM followed by washing with n-pentane and diethyl ether to afford title compound (700 mg, crude TFA salt) as sticky white solid which is used as such for next step. $^1$H-NMR (400 MHz, DMSO): δ 4.19-4.24 (m, 0.5H), 4.27-4.36 (m, 0.5H), 4.48-4.54 (m, 0.5H), 4.60-4.66 (m, 0.5H), 4.90 (t, J=3.64 Hz, 1H), 6.24-6.43 (m, 2H), 6.73 (bs, 1H), 7.84 (d, J=8.44 Hz, 2H), 8.08 (d, J=8.48 Hz, 2H), 8.31 (bs, 3H). LC-MS (m/z): M+H=361.0.

Step-7 Preparation of 2,2-dichloro-N-((1R,2S)-3-fluoro-1-(4-(S-(fluoromethyl) sulfonimidoyl)phenyl)-1-hydroxypropan-2-yl)acetamide

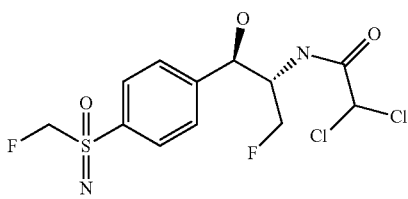 [SMILES: N=S(=O)(CF)c1ccc([C@@H](O)[C@@H](CF)NC(=O)C(Cl)Cl)cc1]

To a solution of (1R,2S)-2-Amino-3-fluoro-1-((N-[(Trifluoroacetyl)methyl phenyl sulfoximine)-propan-1-ol TFA salt (70 mg, 0.194 mmol) in Methanol (10 mL) is added TEA (0.056 mL, 0.389 mmol) followed by addition of ethyldichloroacetate (0.061 mL, 0.389 mmol). The resulting reaction mixture is stirred at room temperature for 16 h. After completion of the reaction, solvent is evaporated in vacuo to get crude which is purified by combi-flash (4 g column) chromatography using 5.7% MeOH in DCM as an eluent to afford title compound (24 mg) as sticky colorless mass. $^1$H-NMR (400 MHz, DMSO) δ: 4.12-4.14 (m, 0.5H), 4.27-4.31 (m, 1H), 4.43 (m, 0.5H), 4.57-4.58 (m, 0.5H), 4.69-4.70 (m, 0.5H), 4.81-4.84 (m, 1H), 4.97-4.99 (m, 1H), 5.20-5.37 (m, 2H), 6.6 (d, J=4.36 Hz, 1H), 6.46 (d, J=1.96 Hz, 1H), 7.61 (d, J=8.28 Hz, 2H), 7.85 (d, J=8.36 Hz, 2H), 8.63 (d, J=8.16 Hz, 1H). LC-MS (m/z): M−H=373.1.

Example 10

Preparation of 2,2-dichloro-N-((1R,2S)-3-fluoro-1-(4-(S-(fluoromethyl)sulfonimidoyl)phenyl)-1-hydroxypropan-2-yl)acetamide Scheme 9

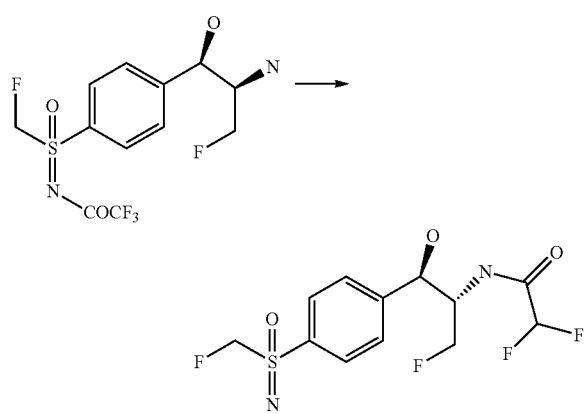

Preparation of 2, -difluoro-N-((1R,S)-3-fluoro-1-(4-(S-(fluoromethyl) sulfonimidoyl)phenyl)-1-hydroxypropan-2-yl)acetamide

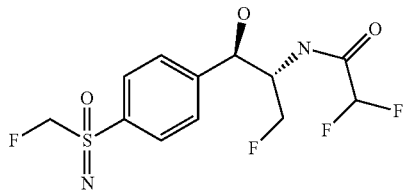 [SMILES: N=S(=O)(CF)c1ccc([C@@H](O)[C@@H](CF)NC(=O)C(F)F)cc1]

To a solution of (1R,2S)-2-Amino-3-fluoro-1-((N-[(Trifluoroacetyl)methyl phenyl sulfoximine)-propan-1-ol TFA salt (350 0.972 mmoll) in Methanol (15 mL) is added TEA (0.281 mL, 1.944 mmol) followed by addition of ethyldifluoroacetate (0.241 mL, 1.944 mmol). The resulting reaction mixture is stirred at room temperature for 16 h. After completion of the reaction, solvent is evaporated in vacuo to get crude which is purified by combi-flash chromatography using 58% ethyl acetate in hexane as an eluent to afford title compound (53 mg) as white solid. $^1$H-NMR (400 MHz, DMSO) δ: 4.35-4.37 (m, 1.5H), 4.41-4.45 (m, 0.5H), 4.53-4.58 (m, 0.5H), 4.65-4.69 (m, 0.5H), 4.84-4.85 (m, 1H), 4.95 (t, J=3.56 Hz, 1H), 5.21-5.42 (m, 2H), 6.08 (d, J=4.44 Hz, 1H), 6.17 (t, J=53.64 Hz, 1H), 7.60 (d, J=8.36 Hz, 2H), 7.87 (d, J=8.32 Hz, 2H), 8.85 (d, J=8.52 Hz, 1H), LC-MS (m/z): M+H=343.1.

We claim:
1. A compound of formula I

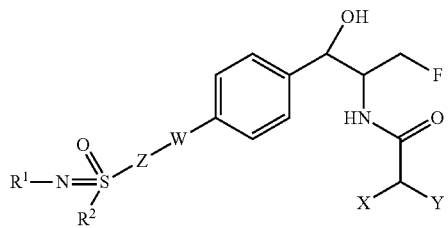

wherein $R^1$ is —H, —C(O)—$R^3$, —$C_1$-$C_6$ alkyl, or —CN;
$R^2$ is -$C_1$-$C_6$ alkyl optionally substituted with one to three halo, or —$C_3$-$C_6$ cyclopropyl;
$R^3$ is —$C_1$—$C_6$ alkyl;
W is

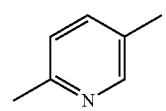

or absent;
X and Y are each independently halo;
Z is —$C_1$-$C_2$ alkyl-, —$C_3$-$C_4$ cycloalkyl- or absent;
or an isomer thereof, or a pharmaceutical acceptable salt thereof.

2. A compound of claim 1 wherein X and Y are each chloro, or X and Y are each fluoro.

3. A compound of claim 1 wherein W is

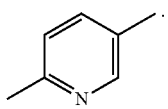

4. A compound of claim 3 of formula II

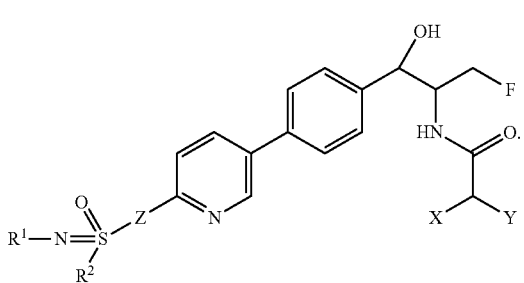

5. A compound of claim 4 wherein $R^1$ is —H or —CN, $R^2$ is —CH$_3$, and Z is —CH$_2$— or absent.

6. A compound of claim 5 selected from the group consisting of:
   2,2-difluoro-N-((1R,2S)-3-fluoro-1-hydroxy-1-(4-(6-(S-methylsulfonimidoyl)-pyridin-3-yl)phenyl)propan-2-yl)acetamide;
   2,2-difluoro-N-{(1S,2R)-1-fluoromethyl-2-hydroxy-2-[4-(6-N-(cyano) methyl pyridine sulfoximine-3-yl)phenyl]-ethyly}-acetamide;
   2,2dichloro-N-((1R,2S)-3-fluoro-1-hydroxy-1-(4-(6-(S-methylsulfonimidoyl)-pyridin-3-yl)phenyl)propan-2-yl)acetamide;
   2, 2-difluoro-N-{(1 S, 2R)-1-fluoromethyl-2-hydroxy-2-[4-(6(S-methylsulfonimidoylmethyl) pyridine-3-yl)-phenyl]-ethyl}-acetamide; and
   2, 2-difluoro-N-{(1 S, 2R)-1-fluoromethyl-2-hydroxy-2-[4- (6-N-[(cyano) methyl]-methyl pyridine sulfoximine-3-yl)-phenyl]-ethyl}-acetamide.

7. A compound of claim 1 wherein W is absent and Z is absent.

8. A compound of claim 7 of formula III

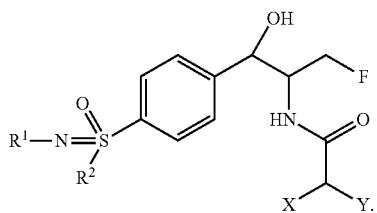

9. A compound of claim 8 wherein $R^1$ is —H or —CN and $R^2$ is —CH$_3$ or —CH$_2$—F.

10. A compound of claim 9 selected from the group consisting of 2, 2-dichloro-N-((1R, 2S)-3-fluoro-1-hydroxy-1-(4-(S-methylsulfonimidoyl) phenyl) propan-2-yl) acetamide;
   2,2-dichloro-N-[(1 S, 2R)-1-fluoromethyl-2-hydroxy-2-(4-(cyano)methyl-phenyl sulfoximine)-ethyl]-acetamide;
   2,2-difluoro-N-[(1 S, 2R)-1-fluoromethyl-2-hydroxy-2-(4-(cyano)methyl-phenyl sulfoximine)-ethyl]-acetamide;
   2,2-dichloro-N-((1R,2S)-3-fluoro-1-(4-(S-(fluoromethyl) sulfonimidoyl) phenyl)-1-hydroxypropan-2-yl) acetamide; and
   2,2-dichloro-N-((1 R, 2S)-3-fluoro-1-(4-(S-(fluoromethyl) sulfonimidoyl) phenyl)-1-hydroxypropan-2-yl) acetamide.

11. A compound of claim 1 wherein W is

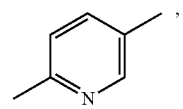

Z is absent, $R^1$ is —H, and $R^2$ is —CH$_3$.

12. A compound of claim 11 of formula IV

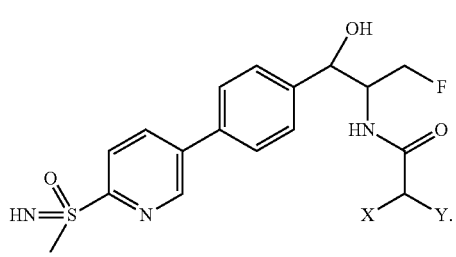

13. A compound of claim 12 wherein X and Y are each chloro or X and Y are each fluoro.

14. A compound of claim 13 selected from the group consisting of:
   2,2-difluoro-N-((1R,2S)-3-fluoro-1-hydroxy-1-(4-(6-(S-methylsulfonimidoyl)-pyridin-3-yl)phenyl)propan-2-yl)acetamide;
   2,2-dichloro-N-((1R,2S)-3-fluoro-1-hydroxy-1-(4-(6-(S-methylsulfonimidoyl)-pyridin-3-yl)phenyl)propan-2-yl)acetamide; and
   2, 2-difluoro-N-{(1 S, 2R)-1-fluoromethyl-2-hydroxy-2-[4-(6(S-methylsulfonimidoylmethyl) pyridine-3-yl)-phenyl]-ethyl}-acetamide.

15. A pharmaceutical composition comprising a compound selected from the group consisting of:
   2,2-difluoro-N-((1R,2S)-3-fluoro-1-hydroxy-1-(4-(6-(S-methylsulfonimidoyl)-pyridin-3-yl)phenyl)propan-2-yl)acetamide;
   2,2-difluoro-N-{(1S,2R)-1-fluoromethyl-2-hydroxy-2-[4-(6-N-(cyano) methyl pyridine sulfoximine-3-yl)-phenyl]-ethyl}-acetamide;
   2,2-dichloro-N-((1R,2S)-3-fluoro-1-hydroxy-1-(4-(6-(S-methylsulfonimidoyl)-pyridin-3-yl)phenyl)propan-2-yl)acetamide;
   2, 2-difluoro-N-{(1 S, 2R)-1-fluoromethyl-2-hydroxy-2 [4-(6-(S-methylsulfonimidoylmethyl) pyridine-3-yl)-phenyl]-ethyl}-acetamide;
   2, 2-difluoro-N-{(1 S, 2R)-1-fluoromethyl-2-hydroxy-2 [4-(6-N-f(cyano) methyl]-methyl pyridine sulfoximine-3-yl)-phenyll-ethyl}-acetamide;
   2, 2-dichloro-N-((1R, 2S)-3-fluoro-1-hydroxy-1-(4-(S-methylsulfonimidoyl) phenyl) propan-2-yl) acetamide;
   2,2-dichloro-N-[(1S, 2R)-1-fluoromethyl-2-hydroxy-2-(4-(cyano)-methyl-phenyl sulfoximine)-ethyl]-acetamide;

2,2-difluoro-N-[(1S, 2R)-1-fluoromethyl-2-hydroxy-2-(4-(cyano)-methyl-phenyl sulfoximine)-ethyl]-acetamide;
2,2-dichloro-N-((1R,2S)-3-fluoro-1-(4-(S-(fluoromethyl) sulfonimidoyl) phenyl)-1-hydroxypropan-2-yl) acetamide; and
2,2-dichloro-N-((1 R, 2S)-3-fluoro-1-(4-(S-(fluoromethyl) sulfonimidoyl) phenyl)-1-hydroxypropan-2-yl) acetamide, or a pharmaceutically acceptable salt thereof and a pharmaceutically acceptable carrier.

16. The composition according to claim 15 wherein the compound is selected from the group consisting of:
2,2-difluoro-N-((1R,2S)-3-fluoro-1-hydroxy-1-(4-(6-(S-methylsulfonimidoyl)-pyridin-3-yl)phenyl)propan-2-yl)acetamide;
2,2-difluoro-N-{(1S,2R)-1-fluoromethyl-2-hydroxy-2-[4-(6-N-(cyano) methyl pyridine sulfoximine-3-yl)-phenyl]-ethyl}-acetamide;
2,2-dichloro-N-((1R,2S)-3-fluoro-1-hydroxy-1-(4-(6-(S-methylsulfonimidoyl)-pyridin-3-yl)phenyl)propan-2-yl)acetamide;
2, 2-difluoro-N-{(1 S, 2R)-1-fluoromethyl-2-hydroxy-2-[4-(6-(S-methylsulfonimidoylmethyl) pyridine-3-yl)-phenyl]-ethyl}-acetamide; and
2, 2-difluoro-N-{(1 S, 2R)-1-fluoromethyl-2-hydroxy-2-[4-(6-N-[(cyano) methyl]-methyl pyridine sulfoximine-3-yl)-phenyl]-ethyl}-acetamide.

17. The composition according to claim 16 wherein the compound is selected from 2,2-difluoro-N-((1R,2S)-3-fluoro-1-hydroxy-1-(4-(6-(S-methylsulfonimidoyl)-pyridin-3-yl)phenyl)propan-2-yl)acetamide or 2, 2-difluoro-N-{(1 S, 2R)-1-fluoromethyl-2-hydroxy-2-[4-(6-(S-methylsulfonimidoylmethyl) pyridine-3-yl)-phenyl]-ethyl}-acetamide.

18. A method for controlling or treating infections in livestock by administering to an animal in need thereof a therapeutically effective amount of a compound selected from the group consisting of:
2,2-difluoro-N-((1R,2S)-3-fluoro-1-hydroxy-1-(4-(6-(S-methylsulfonimidoyl)-pyridin-3-yl)phenyl)propan-2-yl)acetamide;
2,2-difluoro-N-{(1S,2R)-1-fluoromethyl-2-hydroxy-2[-4-(6-N-(cyano) methyl pyridine sulfoximine-3-yl)-phenyl]-ethyl}-acetamide;
2,2-dichloro-N-((1R,2S)-3-fluoro-1-hydroxy-1-(4-(6-(S-methylsulfonimidoyl)-pyridin-3-yl)phenyl)propan-2-yl)acetamide;
2, 2-difluoro-N-{(1 S, 2R)-1-fluoromethyl-2-hydroxy-2-[4-(6-(S-methylsulfonimidoylmethyl) pyridine-3-yl)-phenyl]-ethyl}-acetamide;
2, 2-difluoro-N-{(1 S, 2R)-1-fluoromethyl-2-hydroxy-2[4-(6-N-[((cyano) methyl]-methyl pyridine sulfoximine-3-yl)-phenyl]-ethyl}-acetamide;
2, 2-dichloro-N-((1R, 2S)-3-fluoro-1-hydroxy-1-(4-(S-methylsulfonimidoyl) phenyl) propan-2-yl) acetamide;
2,2-dichloro-N- [(1S, 2R)-1-fluoromethyl-2-hydroxy-2-(4-(cyano)-methyl-phenyl sulfoximine)-ethyl]-acetamide;
2,2-difluoro-N- [(1S, 2R)-1-fluoromethyl-2-hydroxy-2-(4-(cyano)-methyl-phenyl sulfoximine)-ethyl]-acetamide;
2,2-dichloro-N-((1R,2S)-3-fluoro-1-(4-(S-(fluoromethyl) sulfonimidoyl) phenyl)-1-hydroxypropan-2-yl) acetamide; and
2,2-dichloro-N-((1 R, 2S)-3-fluoro-1-(4-(S-(fluoromethyl) sulfonimidoyl) phenyl)-1-hydroxypropan-2-yl) acetamide, or a pharmaceutically acceptable salt thereof.

19. The method of claim 18 wherein the compound is selected from the group consisting of:
2,2-difluoro-N-((1R,2S)-3-fluoro-1-hydroxy-1-(4-(6-(S-methylsulfonimidoyl)-pyridin-3-yl)phenyl)propan-2-yl)acetamide;
2,2-difluoro-N-{(1S,2R)-1-fluoromethyl-2-hydroxy-2-[4-(6-N-(cyano) methyl pyridine sulfoximine-3-yl)-phenyl]-ethyl}-acetamide;
2,2-dichloro-N-((1R,2S)-3-fluoro-1-hydroxy-1-(4-(6-(S-methylsulfonimidoyl)-pyridin-3-yl)phenyl)propan-2-yl)acetamide;
2, 2-difluoro-N-{(1 S, 2R)-1-fluoromethyl-2-hydroxy-2-[4-(6-(S-methylsulfonimidoylmethyl) pyridine-3-yl)-phenyl]-ethyl}-acetamide; and
2, 2-difluoro-N-{(1 S, 2R)-1-fluoromethyl-2-hydroxy-2-[4-(6-N- [((cyano) methyl]-methyl pyridine sulfoximine-3-yl)-phenyl]-ethyl}-acetamide, or a pharmaceutically acceptable salt thereof.

20. The method of claim 19 wherein the compound is selected from from 2,2-difluoro-N-((1R,2S)-3-fluoro-1-hydroxy-1-(4-(6-(S-methylsulfonimidoyl)-pyridin-3-yl)phenyl)propan-2-yl)acetamide or 2, 2-difluoro-N-{(1 S, 2R)-1-fluoromethyl-2-hydroxy-2-[4-(6-(S-methylsulfonimidoylmethyl) pyridine-3-yl)-phenyl]-ethyl}-acetamide, or a pharmaceutically acceptable salt thereof.

* * * * *